US012125087B2

(12) United States Patent
Ketchel, III et al.

(10) Patent No.: US 12,125,087 B2
(45) Date of Patent: Oct. 22, 2024

(54) SELECTIVELY REDEEMABLE BUNDLED SERVICES RECOMMENDER SYSTEMS AND METHODS

(71) Applicant: MDSAVE SHARED SERVICES INC., Brentwood, TN (US)

(72) Inventors: Paul J. Ketchel, III, Brentwood, TN (US); Ani Osborne, Brentwood, TN (US)

(73) Assignee: MDSAVE SHARED SERVICES INC., Brentwood, TN (US)

( * ) Notice: Subject to any disclaimer, the term of this patent is extended or adjusted under 35 U.S.C. 154(b) by 265 days.

(21) Appl. No.: 17/874,273

(22) Filed: Jul. 26, 2022

(65) Prior Publication Data
US 2022/0366471 A1 Nov. 17, 2022

Related U.S. Application Data

(63) Continuation-in-part of application No. 17/560,244, filed on Dec. 22, 2021, now Pat. No. 11,430,036, (Continued)

(51) Int. Cl.
*G06Q 30/00* (2023.01)
*G06Q 10/10* (2023.01)
(Continued)

(52) U.S. Cl.
CPC ......... *G06Q 30/0621* (2013.01); *G06Q 10/10* (2013.01); *G06Q 20/065* (2013.01);
(Continued)

(58) Field of Classification Search
CPC ............. G06Q 30/0621; G06Q 20/065; G06Q 20/10; G06Q 30/0206; G06Q 30/0239; G06Q 30/0613; G06Q 30/0633
See application file for complete search history.

(56) References Cited

U.S. PATENT DOCUMENTS 7,895,061 B2 * 2/2011 Schoenberg ........... G06Q 10/10
705/37
8,494,881 B1 * 7/2013 Wizig ................ G06Q 10/1057
705/3
(Continued)

OTHER PUBLICATIONS

Tolle, Michael A. "A package of primary health care services for comprehensive family-centred HIV/AIDS care and treatment programs in low-income settings." Tropical Medicine & International Health 14.6 (2009): 663-672.*

*Primary Examiner* — Kathleen Palavecino
(74) *Attorney, Agent, or Firm* — Morrison & Foerster, LLP

(57) ABSTRACT

An exemplary healthcare services recommender implementation may be configured to recommend selectively redeemable bundled services comprising care for conditions predicted as likely by a machine learning model based on patient data input. The likely conditions may be predicted for a patient or a patient population comprising a plurality of patients. The machine learning model may comprise a neural network trained to determine a probability distribution of patient condition trends for a future time period based on patient data input. The patient data input may comprise data from an Electronic Medical Record (EMR), diagnosis, lab test, patient-provided information such as survey/symptom data, and/or wearable device data. The machine learning model may be trained using a training data set including at least healthcare outcomes sampled during a past time period from a plurality of patient healthcare episodes each comprising a plurality of procedures performed for the patient in at least one encounter.

30 Claims, 17 Drawing Sheets

Related U.S. Application Data which is a continuation of application No. 17/208,515, filed on Mar. 22, 2021, now Pat. No. 11,244,370, which is a continuation of application No. 16/460,436, filed on Jul. 2, 2019, now Pat. No. 10,991,020, which is a continuation of application No. 14/827,026, filed on Aug. 14, 2015, now abandoned, which is a continuation-in-part of application No. 14/461,209, filed on Aug. 15, 2014, now Pat. No. 9,123,072.

(60) Provisional application No. 61/866,922, filed on Aug. 16, 2013.

(51) Int. Cl.
*G06Q 20/06* (2012.01)
*G06Q 20/10* (2012.01)
*G06Q 20/38* (2012.01)
*G06Q 30/0201* (2023.01)
*G06Q 30/0207* (2023.01)
*G06Q 30/0601* (2023.01)
*G16H 10/60* (2018.01)
*G16H 40/20* (2018.01)
*G16H 70/20* (2018.01)
*G16H 20/00* (2018.01)

(52) U.S. Cl.
CPC ........ *G06Q 20/10* (2013.01); *G06Q 20/381* (2013.01); *G06Q 30/0206* (2013.01); *G06Q 30/0239* (2013.01); *G06Q 30/0613* (2013.01); *G06Q 30/0629* (2013.01); *G06Q 30/0633* (2013.01); *G16H 10/60* (2018.01); *G16H 40/20* (2018.01); *G16H 70/20* (2018.01); *G16H 20/00* (2018.01)

(56) References Cited

U.S. PATENT DOCUMENTS

| | | | |
|---|---|---|---|
| 2007/0043594 A1* | 2/2007 | Lavergne | G06Q 10/10 705/64 |
| 2007/0088580 A1* | 4/2007 | Richards, Jr. | G06Q 40/08 705/4 |
| 2010/0070295 A1* | 3/2010 | Kharraz Tavakol | G16H 40/20 705/2 |
| 2011/0106583 A1* | 5/2011 | Rozell | G06Q 10/02 705/7.29 |
| 2012/0054119 A1* | 3/2012 | Zecchini | G06Q 30/0282 705/347 |
| 2012/0239560 A1* | 9/2012 | Pourfallah | G06Q 20/102 705/40 |
| 2013/0096937 A1* | 4/2013 | Campbell | G16H 40/20 705/2 |
| 2013/0198025 A1* | 8/2013 | Picken | G06Q 30/02 705/26.61 |
| 2014/0067406 A1* | 3/2014 | Hyatt | G06Q 10/10 705/2 |
| 2016/0071225 A1* | 3/2016 | Chmait | G06Q 20/102 705/2 |

\* cited by examiner

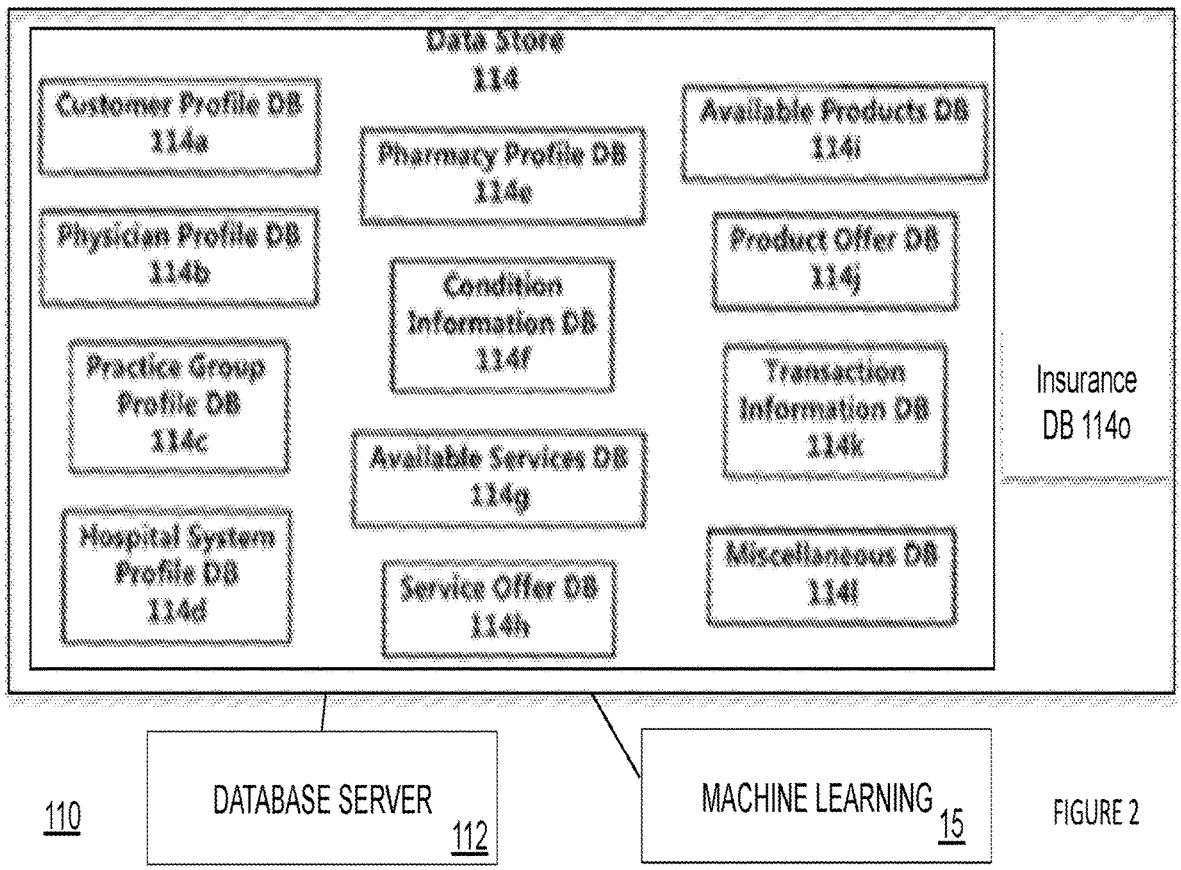
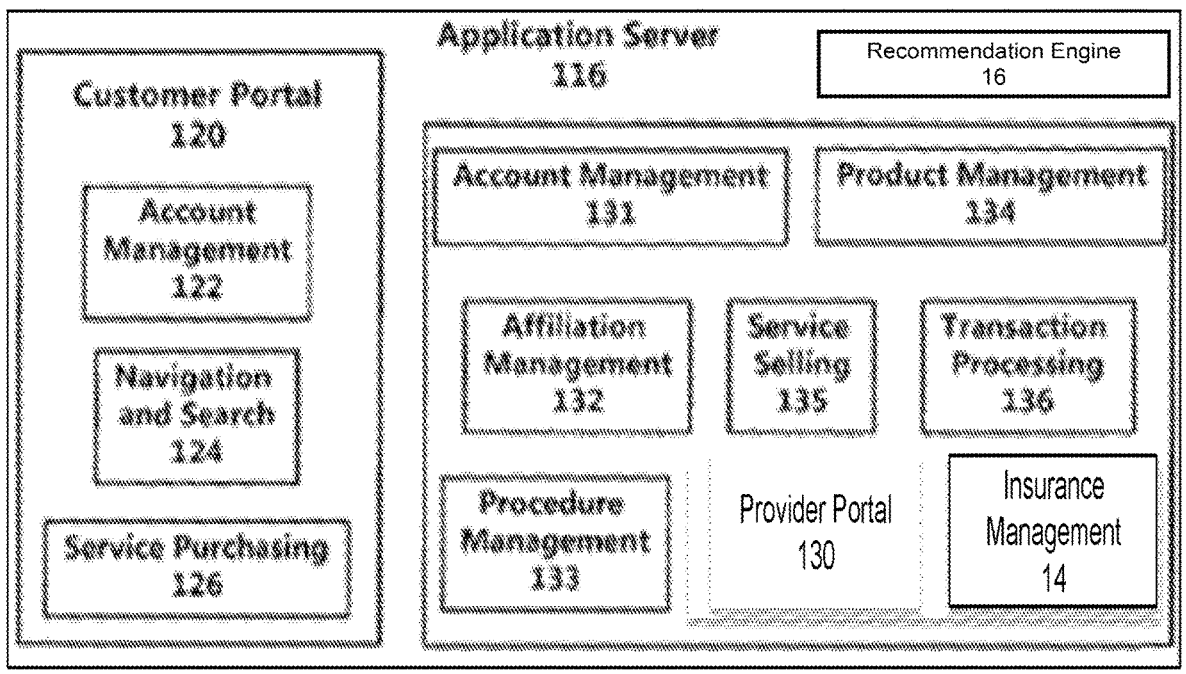
FIGURE 2

Figure 3B

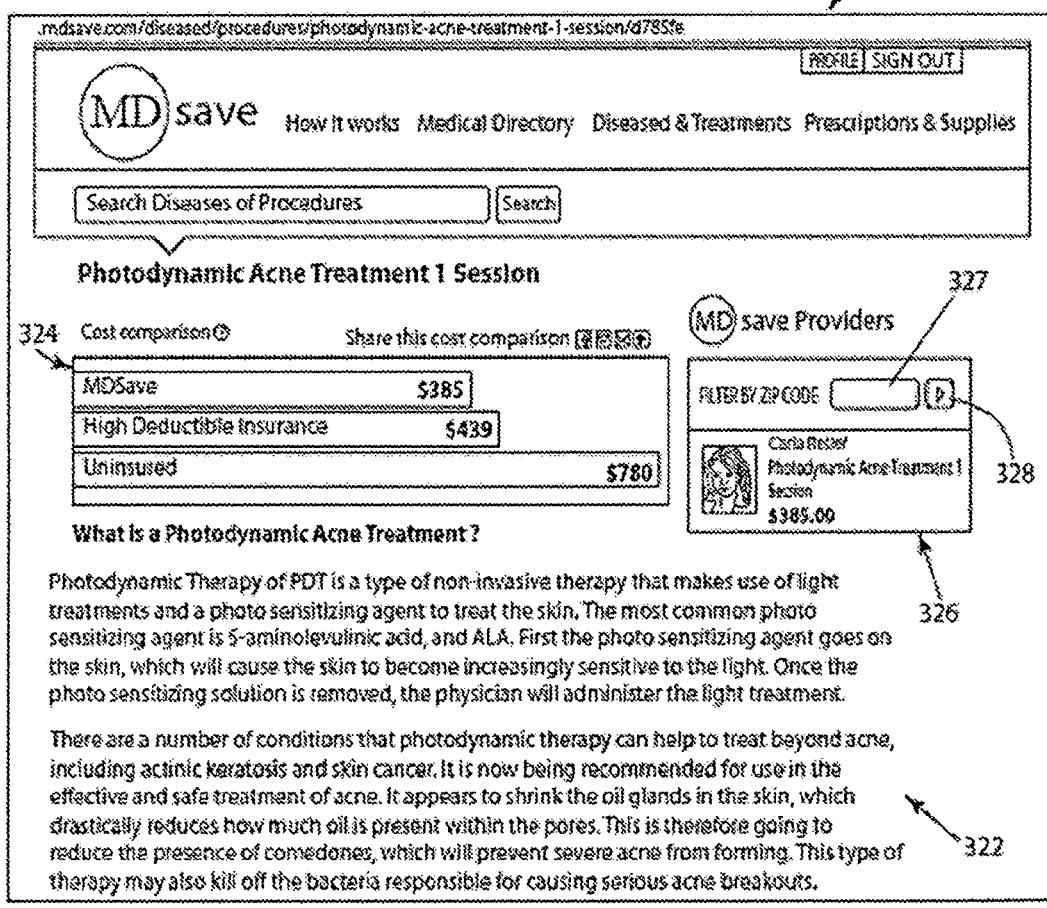

700 702

Radiology ▼

Payout rates listed are suggested rates only. All rates are to be determined by the hospital system.

Specific Locality 704c, 704d                          Recommended Rate — 706

| | | | | | |
|---|---|---|---|---|---|
| Facility | Abilene Medical Center | 0.773 | 704b | Facility | 130% | 706b |
| Physician | REST OF TEXAS | 0.97 | | Physician | 130% | 706a |

704a — 713 — Advanced

☐ Select Mdsave Radiology Group Prking — 712          ∨ Expand all ∧ Collapse all  ☐ Export to Excel — 715

| Procedure | Rec. Facility Price | Rec. Phys. Price | MDsave Fee | Total Amount |
|---|---|---|---|---|
| Bone Densiometry | | | | |
| ∨ Bone Density DXA Extremity | $66.68 | $12.60 | $12.00 | $91.28 |

— 714                708

711 DESCRIPTION        CPT CODE    CMS FACILITY    CMS PHYSICIAN    FACILITY REC RATE 130%    PHYSICIAN REC RATE 130%

| Dxa bone density/peripheral | 77081 | $59.37 | $11.08 | $66.68 | $13.97 |
| Fracture assessment via dxa | 77086 | $59.37 | $8.90 | $66.68 | $11.22 |
| | | | Averages $ | 66.68 | 12.60 |

711b                711a

| Procedure | Rec. Facility Price | Rec. Phys. Price | MDsave Fee | Total Amount |
|---|---|---|---|---|
| > Bone Density DXA Scan | $103.99 | $16.24 | $12.00 | $132.23 |
| Flouroscopy | | | | |
| > Videofluoroscopic Swallowing Study | $114.21 | $126.69 | $60.00 | $300.90 |
| > Barium Enema with air | $169.58 | $64.02 | $60.00 | $293.60 |
| > Barium Swallow | $114.21 | $29.76 | $60.00 | $203.97 |
| > Cyscogram (VCYG) | $297.90 | $78.45 | $60.00 | $436.35 |
| > Fistulogram | $378.52 | $33.82 | $60.00 | $472.04 |
| > Hysterosalpingogram (HSG) Test | $378.52 | $99.64 | $60.00 | $538.16 |
| > Barium Enema | $169.58 | $44.64 | $60.00 | $274.22 |
| Radiology (X-ray) | | | | |
| > X-ray | $64.41 | $13.20 | $12.00 | $89.61 |
| > Complex X-ray | $102.08 | $18.49 | $12.00 | $132.57 |
| CT | | | | |
| > CT Scan With Contrast | $279.65 | $79.66 | $60.00 | $419.31 |
| > CT Scan With & Without Contrast | $314.92 | $84.62 | $60.00 | $459.54 |
| > CT Scan Without Contrast | $142.04 | $69.15 | $60.00 | $271.19 |
| > CT Scan of Abdomen & Pelvis Without Contrast | $271.55 | $112.03 | $60.00 | $443.58 |
| > CT Scan with Myelogram | $689.90 | $59.05 | $60.00 | $808.95 |
| > CT Scan of Abdomen & Pelvis With and Without Contrast | $438.15 | $129.19 | $60.00 | $627.34 |
| > CT Scan of Abdomen & Pelvis With Contrast | $438.15 | $117.00 | $60.00 | $615.15 |
| CTA | | | | |
| > CT Angiography Cardiac Assessment | $249.34 | $134.38 | $60.00 | $443.72 |
| > CT Coronary Angiography | $249.34 | $150.42 | $60.00 | $459.76 |
| > CT Angiography With and Without Contrast | $327.90 | $117.45 | $60.00 | $505.35 |

[ Email Prices ] [ Save Changes ] [ Take Live ]

General Surgery ▼

Payout rates listed are suggested rates only. All rates are to be determined by the hospital system.

Specific Locality   704e   704f                    Recommended Rate
                                         706c
Anesthesia  | NATIONAL RATE |   | 1 |      Anesthesia | 100% |
Facility    | Abilene Medical Center | | 0.773 |  Facility   | 130% |
Physician   | REST OF TEXAS | | 0.97 |      Physician  | 130% |

716                              Advanced
☐ Anesthesis                                  ∨ Expand all ∧ Collapse all ☐ Export to Excel

| Procedure | Rec. Facility Price | Rec. Phys. Price | Rec. Anesthesia. Price | MDsave Fee | Total Amount |
|---|---|---|---|---|---|
| General Surgery | | | | | |
| > Colonoscopy | $877.69 | $334.01 | $250.00 | $125.00 | $1,586.70 |
| ∨ Inguinal Hernia Repair | $3,004.76 | $787.49 | $250.00 | $125.00 | $4,167.25 |

| DESCRIPTION | CPT CODE | CMS FACILITY | CMS PHYSICIAN | CMS ANESTHESIA | FACILITY REC RATE 130% | PHYSICIAN REC RATE 130% | ANESTHESIA REC RATE 100% |
|---|---|---|---|---|---|---|---|
| Repair inguinal hernia, sliding any age | 49525 | $2,675.43 | $590.67 | $250.00 | $3,004.76 | $744.83 | $250.00 |
| Surgical Repair of Inguinal Hernia | 49505 | $2,675.43 | $536.66 | $250.00 | $3,004.76 | $676.75 | $250.00 |
| Repair recurrent inguinal hernia | 49520 | $2,675.43 | $652.17 | $250.00 | $3,004.76 | $822.39 | $250.00 |
| Incarcerated or strangulated | 49521 | $2,675.43 | $739.05 | $250.00 | $3,004.76 | $931.94 | $250.00 |
| Incarcerated or strangulated | 49507 | $2,675.43 | $603.90 | $250.00 | $3,004.76 | $761.52 | $250.00 |
| | | | Averages $ | | 3004.76 | 787.49 | 250.00 |

711b     711a     711c

| > Laparoscopic-assisted vaginal hysterectomy | $6,153.59 | $1,047.82 | $250.00 | $125.00 | $7,576.41 |
| > Appendectomy | $2,567.30 | $836.81 | $250.00 | $125.00 | $3,779.11 |
| > Hysterectomy Ablation | $4,469.00 | $438.69 | $250.00 | $125.00 | $5,282.69 |
| > Total Abdominal Hysterectomy | $0.00 | $1,384.16 | $250.00 | $125.00 | $1,759.16 |
| > Upper Endoscopy (EGD) | $892.54 | $224.78 | $250.00 | $125.00 | $1,492.32 |
| > Vaginal Hysterectomy | $4,469.00 | $1,169.70 | $250.00 | $125.00 | $6,013.70 |
| > Laparoscopic Cholecystectomy (Laparoscopic Gall Bladder Removal) | $4,244.63 | $1,078.63 | $250.00 | $125.00 | $5,698.26 |
| > Laparoscopic Tubal Ligation | $4,244.63 | $914.81 | $250.00 | $125.00 | $5,534.44 |
| > Laparoscopic Appendectomy | $4,244.63 | $782.25 | $250.00 | $125.00 | $5,401.88 |

[ Email Prices ]  [ Save Changes ]  [ Take Live ]

Payout rates listed are suggested rates only. All rates are to be detemined by the hospital system.

Specific Locality                                                   Recommended Rate Facility   Abilene Medical Center   0.773        Facility    130%
Physician  REST OF TEXAS            0.97         Physician   130%
                                          717

○ Anesthesia ● Sedacian ☐ Pathology                    Advanced
                                             ∨ Expand all ∧ Collapse all ☐ Export to Excel

| Procedure | Rec. Facility Price | Rec. Phys. Price | Pathology Price | MDsave Fee | Total Amount |
|---|---|---|---|---|---|
| GI | | | | | |
| › Colonoscopy | $877.69 | $334.01 | $130.00 | $125.00 | $1,466.70 |
| › Flexible Signoidoscopy | $704.39 | $143.19 | $130.00 | $125.00 | $1,102.58 |
| ∨ Transnasal Esophagoscopy [TNE] | $837.38 | $119.03 | $0.00 | $125.00 | $1,081.41 |

| DESCRIPTION | CPT CODE | CMS FACILITY | CMS PHYSICIAN | FACILITY REC. RATE 130% | PHYSICIAN REC. RATE 130% | PATHOLOGY REC. RATE |
|---|---|---|---|---|---|---|
| Esophagoscopy flex doc brush | 43197 | $745.60 | $85.81 | $837.38 | $108.21 | $0.00 |
| Esophagoscopy flex tmsn biopy | 43198 | $745.60 | $102.97 | $837.38 | $129.03 | $0.00 |
| | | Averages $ | | 837.38 | 119.03 | 0.00 |
| | | | | | $125.00 | 711d |

| Procedure | Rec. Facility Price | Rec. Phys. Price | Pathology Price | MDsave Fee | Total Amount |
|---|---|---|---|---|---|
| › Esophageal Manometry | $369.20 | $91.98 | $0.00 | $125.00 | $586.18 |
| › Hemorrhoid Banding | $496.98 | $249.32 | $0.00 | $125.00 | $871.30 |
| › Bravo 48 Hour PH Monitor | $369.20 | $107.31 | $0.00 | $125.00 | $601.51 |
| › Abdominal Paracentesis | $549.59 | $120.15 | $130.00 | $125.00 | $924.74 |
| › Hemorrhoidectomy | $2,180.41 | $513.44 | $0.00 | $125.00 | $2,818.85 |
| › Feeding Tube Placement | $219.23 | $62.22 | $0.00 | $125.00 | $406.45 |
| › Capsule Endoscopy | $957.36 | $246.17 | $0.00 | $125.00 | $1,328.53 |
| › Feeding Tube Placement (PEG) | $1,195.94 | $275.48 | $0.00 | $125.00 | $1,596.42 |
| › Upper Endoscopy (EGD) | $892.54 | $224.78 | $0.00 | $125.00 | $1,242.32 |
| › EGD with Colonoscopy | $1,203.96 | $736.42 | $0.00 | $125.00 | $2,065.38 |

Email Prices   Save Changes   Take Live

Fig. 7C

SELECTIVELY REDEEMABLE BUNDLED SERVICES RECOMMENDER SYSTEMS AND METHODS

CROSS REFERENCE TO RELATED APPLICATIONS

This application is a Continuation-in-part of U.S. application Ser. No. 17/560,244 filed Dec. 22, 2021, which is a Continuation of U.S. application Ser. No. 17/208,515 filed Mar. 22, 2021, now U.S. Pat. No. 11,244,370 issued Feb. 8, 2022, which is a Continuation of U.S. application Ser. No. 16/460,436 filed Jul. 2, 2019, now U.S. Pat. No. 10,991,020 issued Apr. 27, 2021, which is a Continuation of U.S. application Ser. No. 14/827,026 filed Aug. 14, 2015, which is a Continuation-in-part of U.S. application Ser. No. 14/461,209 filed Aug. 15, 2014, now U.S. Pat. No. 9,123,072 issued Sep. 1, 2015, which claims the benefit of U.S. Provisional Patent Application Ser. No. 61/866,922 filed Aug. 16, 2013, the contents of all of which are incorporated herein in their entirety by reference thereto.

BACKGROUND OF THE INVENTION

Exemplary embodiments of the present invention relate to the marketing and facilitating the sale of services and products. More specifically, exemplary embodiments relate to methods and apparatuses for providing a web-based mechanism allowing prospective patients to search for and compare healthcare services and products offered by local providers, including bundled sets of services and sets of one or more services and one or more products, and facilitating prepaid purchases of such healthcare services and products by prospective patients at discounted rates.

The price of healthcare services varies depending on specialty, procedure, and physician practice. In the United States, many patients do not have access to a simple way to shop and compare the price of common medical procedures. Due to the current managed care based system in the US, the cost of treatment is often determined by managed care organizations. These managed care organizations have specific formularies for drugs and procedures designed specifically to patients' individual health plans, which restrict the drugs and procedures available to patients in their particular plans. Currently prospective patients who chose to compare medical costs are forced to conduct extensive, often inefficient, and time consuming research to compare medical procedures prior to treatment.

Healthcare costs continue to outpace pace inflationary growth, provider reimbursement rates continue to fall, and the cost of patient insurance premiums are increasing. These high deductible plans require patients to pay cash payments for medical services until the high deductible is satisfied, and once this deductible has been met, the insurance carrier begins to cover medical costs. As a result, many patients are seeing exponential increases in out-of-pocket expenses for medical procedures and services. As the number of patients who are uninsured, underinsured, or on high deductible plans grows, the need for a mechanism that allows patients to find affordable medical services increases.

SUMMARY OF THE INVENTION

An exemplary healthcare services recommender implementation may be configured to recommend selectively redeemable bundled services comprising care for conditions predicted as likely by a machine learning model based on patient data input. The likely conditions may be predicted for a patient or a patient population comprising a plurality of patients. The machine learning model may comprise a neural network trained to determine a probability distribution of patient condition trends for a future time period based on patient data input. The patient data input may comprise data from an Electronic Health Record (EHR), Electronic Medical Record (EMR), diagnosis, lab test, patient-provided information such as survey/symptom data, and/or wearable device data. The machine learning model may be trained using a training data set including at least healthcare outcomes sampled during a past time period from a plurality of patient healthcare episodes each comprising a plurality of procedures performed for the patient in at least one encounter.

An exemplary implementation may use a trained machine learning model to predict likely conditions and recommend care/tests to be performed for the likely conditions. Given the predictions of likely conditions determined by the machine learning model, an exemplary recommendation engine may recommend care/tests that optimize a healthcare result parameter. For example, the healthcare result parameter may be outcome or cost. An implementation may be configured to recommend care/tests for likely conditions that will optimize outcome based on recommending specific providers based on cost and quality data. An exemplary recommendation engine implementation may be configured to determine care pathways that optimize cost. For example based on patient condition trends predicted by the machine learning model a particular patient may be likely to improve without surgery. The recommender engine may be configured to suggest reevaluating the condition trends for the patient after recommended physical therapy, and optionally recommending surgery if the patient's condition is more severe or if the condition does not improve within a predetermined time period.

An exemplary recommender engine implementation may be configured to implement optimal care pathways using smart contracts for recommended bundled services. For example, an exemplary recommender engine may be configured to proactively offer and/or acquire existing smart contracts for the needed set of procedures, given the care medically indicated for likely conditions predicted by the machine learning model. An exemplary implementation may be configured to process such smart contract acquisitions for bundled services across a population. In an illustrative example, the recommender system may be used by an insurer to predict which procedures would be needed to optimize the health of their member population, permitting the insurer to offer/acquire smart contracts for the needed services in bulk. For example, given ten patients that are predicted by the machine learning model as likely to need shoulder surgery based on their health data, a payer could offer a smart contract for all of those surgeries to providers, based on or adjusting price due to provider quality outcomes. The smart contract may include price adjustments if the number of patients is lower or higher than predicted. Results and outcomes may be used to improve the algorithm, based on training an updated machine learning model using post-procedure healthcare outcome and patient condition data in an updated training data set. A machine learning model trained using bundled services outcome and related patient condition data proprietary to the organization that trained the model may be provided to a third party for further training using outcome and related patent condition data proprietary to the third party.

An exemplary implementation of the present invention may be an apparatus configured for facilitating purchases of services offered by service providers. The apparatus includes an application server providing a network service that is accessible to a plurality of users through a plurality of client systems communicatively coupled to the application server via a network and a data storage system storing a service offer database that is maintained by the application server. The service offer database comprises a plurality of service offer information records respectively associated with a plurality of service offers. The plurality of service offers includes at least one service offer for a bundled set of services. Each service offer information record comprises an indication of a primary service of the associated service offer, a purchase price for the associated service offer, a payment amount for the primary service, and compensation information for the primary service. Upon receiving purchase information for the user for purchasing the selected service offer from the client system, the network service is operable to process a purchase of the selected service offer by the user.

In an exemplary implementation, each service offer for a bundled set of services comprises a bundled set of healthcare services provided by corresponding healthcare service providers. In exemplary embodiments, at least one service offer information record associated with a service offer for a bundled set of services further comprises an indication of a facility for performing the primary service, a facility fee for the facility, and compensation information for the facility fee. In an exemplary implementation, at least one service offer information record associated with a service offer for a bundled set of services further comprises an indication that at least one of the secondary services associated with the primary service is an optional secondary service. The network service is further operable to receive an indication from the user of the client system, for each optional secondary service of the service offer, of whether the optional secondary service is to be included in the purchase of the selected service offer.

In an exemplary implementation, the data storage system stores a customer profile database allows users to register on providing personal information for purchasing healthcare services; a physician profile database to maintain records of individual physician offering healthcare services; a condition information database to maintain information records for various health conditions and diseases for which corresponding healthcare services are offered; a hospital system profile database to maintain account information records for hospital system administrator providing pre-paid healthcare services; an available service database to maintain records of various healthcare services offered by at least one of: a physician; and a hospital; and a transaction information database to maintain records of purchases made by registered users.

In an exemplary implementation, the network service, upon being accessed by a user of one of the client systems to process a purchase of a service offer, generates a voucher for the user that specifies a unique confirmation number for the purchase and the corresponding service provider for each of the service.

The above-described and other features and advantages realized through the techniques of the present disclosure will be better appreciated and understood with reference to the following detailed description, drawings, and appended claims. Additional features and advantages are realized through the techniques of the present invention. Other embodiments and aspects of the invention are described in detail herein and are considered a part of the claimed invention.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description of exemplary embodiments of the present invention taken in conjunction with the accompanying drawings in which:

FIG. 2 is a block diagram illustrating a server system in accordance with an exemplary embodiment of the present invention;

FIGS. 3A-3D are a number of screen shots illustrating examples of a graphical user interfaces that may be implemented by services provided within a customer portal in accordance with exemplary embodiments of the present invention;

FIGS. 7A-7C are a number of screen shots illustrating examples of a graphical user interfaces that may be implemented by services provided within a provider portal in accordance with exemplary embodiments of the present invention.

Figure 1:
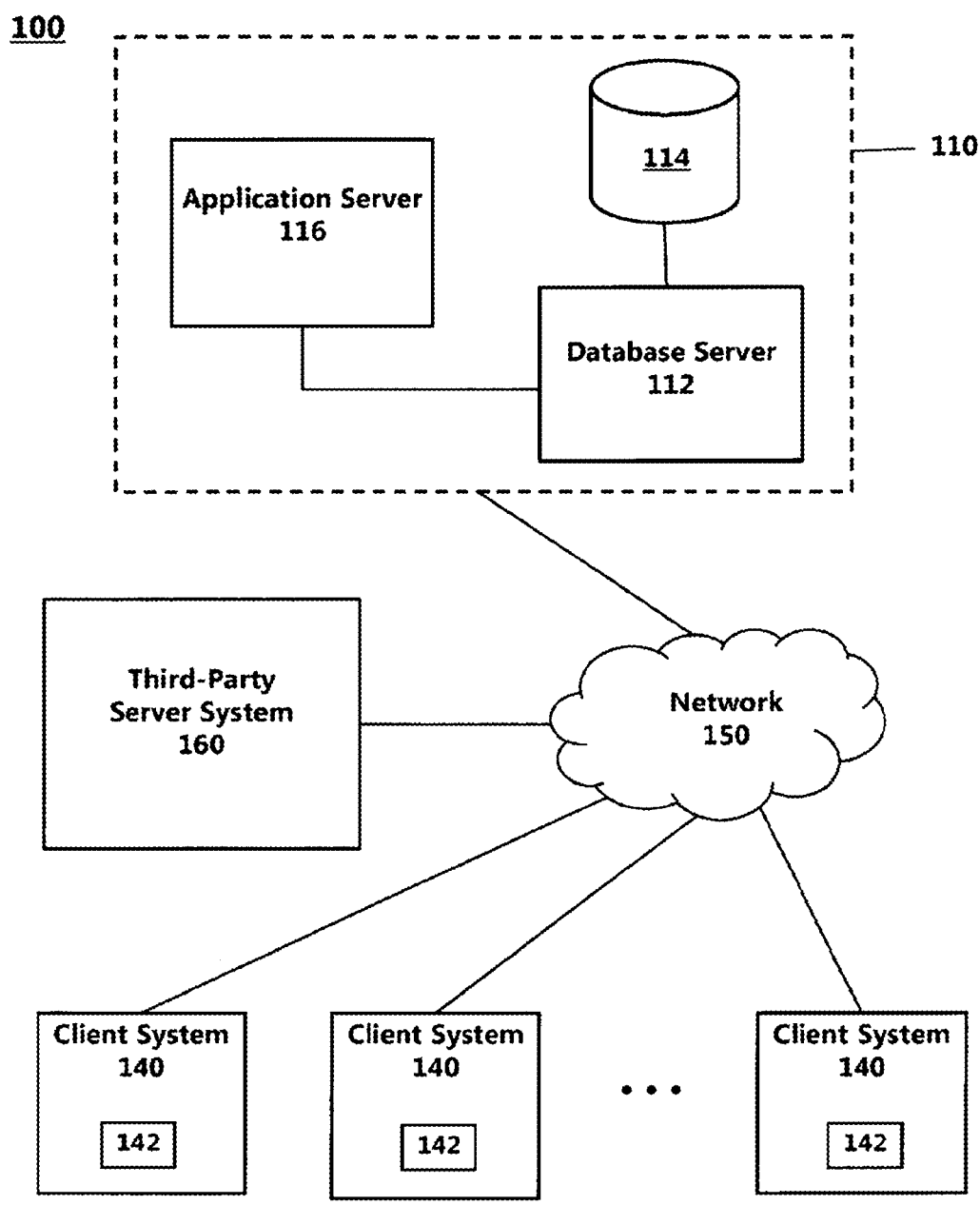
FIG. 1 is a schematic diagram illustrating an example network architecture for a healthcare marketplace system that can be configured to implement exemplary embodiments of the present invention.

The detailed description explains exemplary embodiments of the present invention, together with advantages and features, by way of example with reference to the drawings, in which similar numbers refer to similar parts throughout the drawings. The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered to be within the scope of the claimed invention.

DETAILED DESCRIPTION

While the specification concludes with claims defining the features of the invention that are regarded as novel, it is believed that the invention will be better understood from a consideration of the description of exemplary embodiments in conjunction with drawings. It is of course to be understood that the embodiments described herein are merely exemplary of the invention, which can be embodied in various forms. Therefore, specific structural and functional details disclosed in relation to the exemplary embodiments described herein are not to be interpreted as limiting, but merely as a representative basis for teaching one skilled in the art to variously employ the present invention in virtually any appropriate form, and it will be apparent to those skilled in the art that the present invention may be practiced without these specific details. Further, the terms and phrases used herein are not intended to be limiting but rather to provide an understandable description of the invention.

Exemplary embodiments of a transactional marketplace system in accordance with the present invention will now be described with reference to the drawings. Exemplary embodiments of the present invention may be implemented to provide healthcare service providers and pharmacies with a mechanism to remotely offer healthcare services and products to prospective patients at discounted rates in exchange for prepayment of the costs for the services and products via a network-based application (for example, a web-based application). In this regard, exemplary embodiments may further be implemented to provide prospective patients with a mechanism to remotely search, compare, and make pre-paid purchases of such healthcare services and products offered by local medical service providers and pharmacies via a network-connected device configured to access the network-based application. Exemplary embodiments may be further implemented to provide healthcare service providers with the ability to remotely offer a bundled set of healthcare services that are performed separately by multiple providers or a bundled set of one or more healthcare services and one or more products to prospective patients through such a network-based mechanism in which the patient is provided the opportunity to make a prepaid purchase of such a bundled set of service(s) and/or product(s) in a single transaction via the network-connected device, whereby the network-based application facilitates a disbursed distribution of the payment among the multiple healthcare service providers that perform services or sell products included in the bundled set.

Exemplary embodiments may be further implemented to provide various types of healthcare service providers, which may include individual physicians, practice groups, hospital systems, and pharmacies, with the ability to establish affiliations with one another through such a network-based mechanism and provide various options allowing the service providers to remotely offer healthcare services and products in association with these affiliations.

It should further be noted that various aspects of exemplary embodiments of the present invention described herein are not limited to healthcare services (also referred to herein as procedures) and products but, rather, may be implemented with respect to any suitable classes and types of services and products that may be offered by any suitable classes and types of service providers and retailers that would benefit from bundling, shopping and paying for diverse services from diverse sources.

Referring now to FIG. 1, a schematic diagram illustrating an example network architecture for a healthcare marketplace system 100 configured to implement exemplary embodiments of the present invention is provided. It should of course be understood that FIG. 1 is intended as an example, not as an architectural limitation for different embodiments of the present invention, and therefore, the particular elements depicted in FIG. 1 should not be considered limiting with regard to the environments within which exemplary embodiments of the present invention may be implemented.

In the example illustrated in FIG. 1, healthcare marketplace system 100 is implemented as a client/server system that includes a central server system 110 that is commonly accessed by each user of the system through operation of any of a plurality of client systems 140 that are operatively coupled to the central server system via a communication network 150. Central server system 110 further includes a database server 112 coupled to a data store 114, a machine learning module 15 and an application server 116, and each client system 140 is a user terminal or other client device implementing software for and running a respective client application 142 for accessing services provided via a network-based application (also referred to herein as a network service) implemented by application server 116. Such client applications may also be referred to as client modules, or simply clients, and may be implemented in a variety of ways. In exemplary embodiments, such client applications can be implemented as any of a myriad of suitable client application types, which range from proprietary client applications (thick clients) to web-based interfaces in which the user agent function is provided by a web server and/or a back-end program (for example, a CGI program). In the depicted implementation the application server 116 includes the recommendation engine 16. In the depicted central server system 110 implementation the application server 116 is communicatively and operably coupled with the database server 112, the data store 114 and the machine learning module 15.

As further illustrated, exemplary marketplace system 100 may also include at least one third-party server system 160 to enable other functionality that may be accessed and utilized by server system 110 to provide and/or enhance the network service discussed herein. In exemplary embodiments, marketplace system 100 can include additional servers, clients, and other devices not shown in FIG. 1. In exemplary embodiments, network 150 can be configured to facilitate communications between server system 110 and client systems 140, as well as communications with and between other devices and computers connected together within marketplace system 100, by any suitable wired (including optical fiber), wireless technology, or any suitable combination thereof, including, but not limited to, personal area networks (PANs), local area networks (LANs), wireless networks, wide-area networks (WAN), the Internet (a network of heterogeneous networks using the Internet Protocol, IP), and virtual private networks, and the network may also utilize any suitable hardware, software, and firmware technology to connect devices such as, for example, optical fiber, Ethernet, ISDN (Integrated Services Digital Network), T-1 or T-3 link, FDDI (Fiber Distributed Data Network), cable or wireless LMDS network, Wireless LAN, Wireless PAN (for example, IrDA, Bluetooth, Wireless USB, Z-Wave and ZigBee), HomePNA, Power line communication, or telephone line network. Such a network connection can include intranets, extranets, and the Internet, may contain any number of network infrastructure elements including routers, switches, gateways, etc., can comprise a circuit switched network, such as the Public Service Telephone Network (PSTN), a packet switched network, such as the global Internet, a private WAN or LAN, a telecommunications network, a broadcast network, or a point-to-point network, and may utilize a variety of networking protocols now available or later developed including, but not limited to the Transmission Control Protocol/Internet Protocol (TCP/IP) suite of protocols for communication.

In exemplary embodiments, application server 116, database server 112, and any other servers employed within server system 110 and third-party servers utilized within marketplace system 100 can be implemented within any suitable computing system or systems such as a workstation computer, a mainframe computer, a server system (for example, SUN ULTRA workstations running the SUN operating system, IBM RS/6000 workstations and servers running the AIX operating system, or an IBM zSeries eServer running z/OS, zNM, or LINUX OS), a server cluster, a distributed computing system, a cloud based computing system, or the like, as well as any of the various types of computing systems and devices described below with reference to the client systems 140. Server system 110 may be implemented using any of a variety of architectures. For example, application server 116 and database server 112 may also be implemented independently or as a single, integrated device. While the exemplary embodiment illustrated in FIG. 1 depicts application server 116 and database server 112 as individual components, the applications provided by these servers, or various combinations of these applications, may actually be server applications running on separate physical devices. In this regard, server system 110 may comprise a number of computers connected together via a network and, therefore, may exist as multiple separate logical and/or physical units, and/or as multiple servers acting in concert or independently, wherein each server may be comprised of multiple separate logical and/or physical units. In exemplary embodiments, server system 110 can be connected to network 150 through a collection of suitable security appliances, which may be implemented in hardware, software, or a combination of hardware and software.

As illustrated in FIG. 1, application server 116 is communicatively coupled to database server 112. Database server 112 is connected to data store 114, which comprises a plurality of databases that are maintained by database server 112, accessed by application server 116 via database services provided at a front end by database server 112, and store information on a variety of matters that is utilized in providing the services offered via the network service provided by the application server, as described below in greater detail.

In the exemplary implementation depicted by FIG. 2 the recommendation engine 16 may instruct the service offer database 114h to store each healthcare service provider service corresponding to the user selection. The user selection may comprise patient data inputs and preferences of the user. One or more machine learning algorithm configured in the machine learning module 15 may be trained using patient data inputs, user preferences and available procedures to identify the best results/hits based on the user selection. The recommendation engine 16 may be configured to display via the graphical user interface/provider portal 130 the bundled set of service offers that best match the users' selection according to the best results/hits identified by the machine learning module 15. In an exemplary implementation the machine learning module 15 may comprise one or more machine learning algorithm trained to take into account multiple user input parameters such as but not limited to type of disease, medical test results, procedure outcome, patient wellness, location, provider expertise, procedures, hospitals, and pricing. One or more machine learning algorithm configured in the machine learning module 15 may be trained to predict one or more procedure likely to be needed by a patient based on the patient data input to the one or more machine learning algorithm. A recommendation engine 16 implementation may be configured to recommend one or more needed procedure based on a prediction by the one or more trained machine learning algorithm determined as a function of the patient data input.

An exemplary machine learning module 15 may be configured to employ any type of machine-learning algorithm, such as neural networks, expert systems, Bayesian belief networks, decision trees, random forests, regression models, fuzzy logic, data fusion engines and the like. The recommendation engine 16 may employ combinations of various artificial intelligence techniques to recommend a healthcare service using the service offer database 114h and the machine learning module 15. In an illustrative example, the one or more machine learning algorithm configured in the machine learning module 15 may comprise computational models designed to emulate human learning. Some machine learning models are designed to imitate the structure and function of at least parts of a human brain, using densely interconnected information transformation elements. Such dense interconnections among information processing elements permit the one or more machine learning model to be trained to recognize or understand complex output to input relationships defined by the model training data set and training process. For example an artificial neural network is an adaptable machine learning model that may be structurally changed during a learning or training phase, based on input data and feedback concerning the output from the neural network. As a result of feedback during the training, the neural network may be updated to correct an error made by the network during the training. For example some characteristics or parameters of the structures or compositions interposed between the inputs and outputs of artificial neural networks may be known as weights and biases. In some examples of neural network training, the output determined as a function of a given input may be changed to match the desired output by adapting the weights or biases. In some neural network training, historical data may be provided to a trainee neural network as input data, and the output compared to the desired response. Some neural networks may be trained in multiple training passes repeated until a desired error rate for the trainee neural network is achieved. In some examples, trained neural networks may be evaluated based on a comparison of the trainee neural network's prediction accuracy to the prediction accuracy of previously validated neural networks. The prediction accuracy of a trained neural network may be evaluated by comparison to the prediction accuracy of previously validated neural networks based on a procedure known as cross-validation. Some learning machines may be validated after or during training through testing the learning machine's predictions or estimates based on test data. Some cross-validation procedures may reserve a subset of data for training, and another subset of data for test.

With continuing reference to FIG. 2, a block diagram illustrating an exemplary embodiment of server system 110 is provided. As illustrated in FIG. 2, application server 116 is implemented to provide a plurality of services via a customer portal 120 and a plurality of services via a provider portal 130. As described herein, application server 116 can be implemented to provide a respective set of services for each of various types of users (for example, unregistered guests, customers, individual physicians, nurses, office staff, practice group administrators, hospital system administrators, pharmacy administrators, and the like), and some of the services offered by application server 116 can be commonly applicable to and accessible by all types of users, while other services can be applicable to and accessible only by specific types of users. For purposes of description, the terms "providers" and "provider users" are used herein to refer to the general class of users that register with the system to offer healthcare services or products for purchase by customer users registered with the system. As further illustrated in exemplary embodiment of FIG. 2, and as will described in greater detail below, the services provided via customer portal 120 include a registration and account management service 122, a navigation and search service 124, and a purchasing service 126, and the services provided via provider portal 130 include a registration and account management service 131, an affiliation management service 132, a procedure management service 133, a product management service 134, a service selling service 135, an insurance management 14 and a transaction processing service 136.

As further illustrated in exemplary embodiment of FIG. 2, a data store 114 comprises a plurality of databases that are maintained and accessible by application server 116 via database server 112, including a customer profile database 114a, a physician profile database 114b, a practice group profile database 114c, a hospital system profile database 114d, a pharmacy profile database 114e, a condition information database 114f, an available services database 114g, a service offer database 114h, an available products database 114i, a product offer database 114j, a transaction information database 114k, one or more additional databases 114l, and an insurance database 114o that may be used for storing any other suitable information that may be utilized by server system 110 (for example, system usage data, audit trail data, data used internally within the system by application server 116, and the like). In the present exemplary embodiment, customer profile database 114a is used to maintain account information records for customer users that register with server system 110 to purchase healthcare services and products being offered by provider users registered with the system. For each customer for which an account is registered with server system 110, various items of information relevant to the customer, such as name, address or location information, contact information, billing information, and any other suitable identifying information, as well as a unique user name and password associated with the account that can be used to log into the account, can be included in the respective account information record for the customer that is maintained within customer profile database 114a. The account information record for each customer can also be associated with a unique customer account identifier within customer profile database 114a that is used by application server 116 for performing various operations.

Physician profile database 114b is used to maintain account information records for individual physician users that register with server system 110 to offer healthcare services for purchase by customer users registered with the system, as well as account information records for individual physicians that are registered with the system in association with a practice group or hospital system (as described in greater detail below). For each physician for which an account is registered with server system 110, various items of information relevant to the physician, such as name, practice specialty, office location(s) and hours, a profile picture, contact information, biographical information (such as awards, honors, publications, patient testimonials, and other information that can be helpful for marketing the physician to customers accessing the system), URLs or references to websites and social media profiles, group practice and hospital affiliation(s), pharmacy affiliation(s) (for example, on-site pharmacies at facilities or clinics that the physician uses for patient visits or particular procedures), outside facilities that are used for particular procedures performed by the physician (for example, particular hospitals or clinics), compensation information (indicating a financial account for receiving payment for purchases of services offered by the physician via the system and, in some embodiments, a financial account for receiving payment for purchases of products offered by affiliated pharmacies via the system, which may be the same as or different than the financial account specified for receiving payment for purchases of services), and any other suitable identifying information, as well as a unique user name and password associated with the account that can be used to log into the account, may be included in the respective account information record for the physician that is maintained within physician profile database 114b. The account information record for each physician can also be associated with an account status and a unique physician account identifier within physician profile database 114b that is used by application server 116 for performing various operations.

Practice group profile database 114c is used to maintain account information records for practice group administrator users that register with server system 110 to offer healthcare services provided by physicians affiliated with a practice group for purchase by customer users registered with the system. For each practice group for which an account is registered with server system 110, various items of information relevant to the practice, as disclosed in the physician profile database 114b.

Hospital system profile database 114d is used to maintain account information records for hospital system administrator users that register with server system 110 to make on-site, in-person sales of pre-paid healthcare services provided by physicians affiliated with a hospital system for purchase by patients operating client systems within marketplace system 100. For each hospital system for which an account is registered with server system 110, various items of information relevant to the hospital system, such as practice group and physician affiliation(s), pharmacy affiliation(s) (for example, on-site pharmacies at facilities or clinics that affiliated physicians or practice groups use for patient visits or particular procedures), facilities that are used for particular procedures performed by physicians affiliated with the hospital system, compensation information (indicating a financial account for receiving payment for purchases of services offered by affiliated physicians via the system and, in some embodiments, a financial account as disclosed in physician profile database 114b. Pharmacy profile database 114e is used to maintain account information records for pharmacy administrator users that register with server system 110 to offer healthcare products, such as prescription drugs and medical supplies, for purchase by customer users registered with the system, through a particular pharmacy. For each pharmacy for which an account is registered with server system 110, various items of information relevant to the pharmacy, an indication of whether the pharmacy has agreed to accept vouchers for or otherwise honor pre-paid purchases of healthcare products made by customer users via healthcare marketplace system 100 (as will be discussed in greater detail below), and any other suitable identifying information, as well as a unique user name and password associated with the account that can be used to log into the account, may be included in the respective account information record for the pharmacy that is maintained within pharmacy profile database 114e.

Condition information database 114f is used to maintain information records for various health conditions and diseases for which corresponding healthcare services and products (for example, tests, treatments, and drugs) that can be offered by providers registered with server system 110 for purchase by customer users registered with the system. In exemplary embodiments, the various conditions and diseases for which respective information records are maintained in condition information database 114f and the information that populates the respective information record for each condition or disease can be created and maintained by a back-end administrator of server system 110. For each condition or disease for which an information record is created, various items of information relevant to the condition or disease, such as name, description, causes, risk factors, symptoms, common treatments, corresponding healthcare services and products that can be offered by providers registered with server system 110 (for example, each associated healthcare service may be identified within the information record using a unique procedure identifier that is used to identify an information record for the service within available services database 114g, and each associated healthcare product may be identified within the information record using a unique product identifier that is used to identify an information record for the product within available products database 114i, as discussed below), and any other suitable information may be included in the respective information record for the condition or disease that is maintained within condition information database 114f.

Available services database 114g is used to maintain information records for various healthcare services (for example, tests and treatments) that can be offered by providers registered with server system 110 for purchase by customer users registered with the server system. For each service for which an information record is created, various items of information relevant to the service, such as name, procedure detail, one or more medical specialties with which the procedure is commonly associated, any healthcare products (for example, drugs or medical supplies) with which the procedure is commonly associated, cost information (for example, average prices for the service for patients that are uninsured and/or have a high deductible insurance plan and an average price for purchasing the service that is offered by providers registered with server system 110), a medical code number identifying the service according to the nomenclature used by a formal medical classification system (for example, a code that is used to identify the service according to the Current Procedural Terminology (CPT) code set), a unique procedure identifier that is used by application server 116 to uniquely identify the particular service, and any other suitable information may be included in the respective information record for the service that is maintained within available services database 114g.

Figure 8:
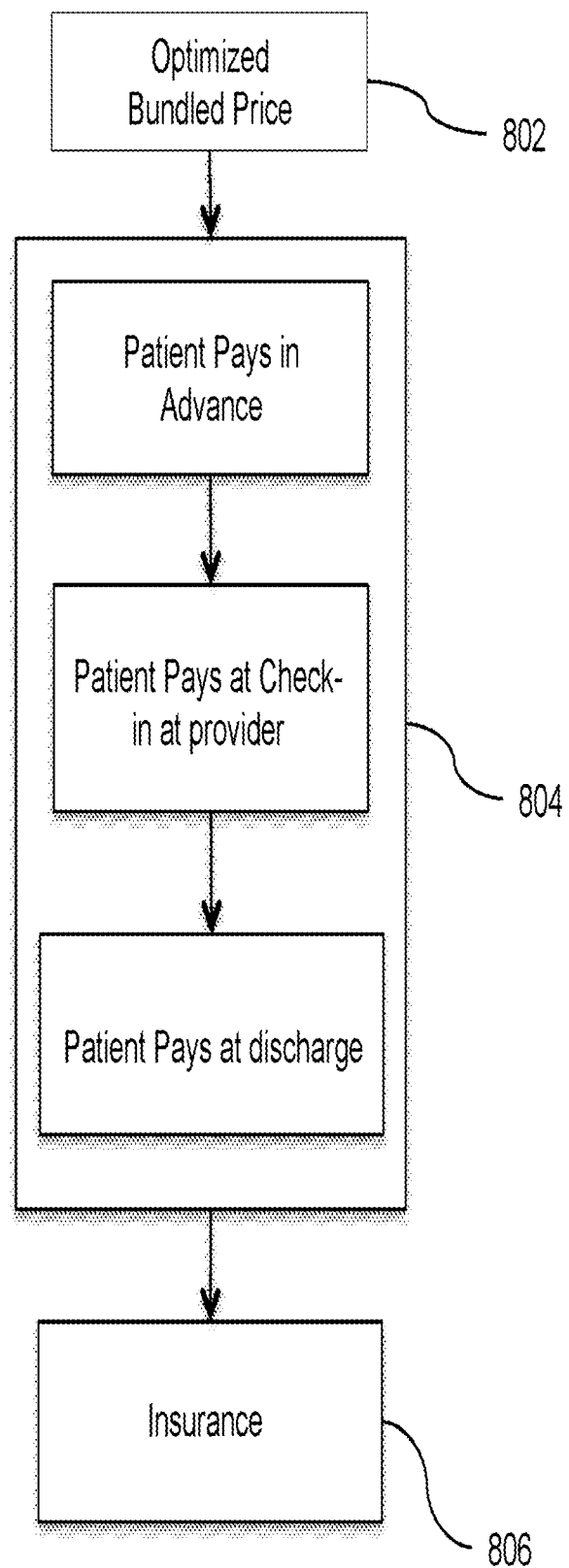
FIG. 8 illustrates a flow chart of an insurance policy stored in the insurance database executed by the application server in accordance with exemplary embodiments of the present invention.

The insurance database 114o and the insurance management 14 are explained in detail in conjunction with FIG. 8 of the present invention. Additionally, in exemplary embodiments, the information record for each service that is maintained within available services database 114g may further include an indication of whether the service can be offered by providers within marketplace system 100 as an individual primary service or as a primary service of a bundled set of a plurality of services or one or more services and one or more products (for which a single payment for the bundled set will be disbursed to different provider for each of the services and products in the bundled set). Such items of information relevant to the bundled set included in the respective information record for a primary service may include, for example, items of information describing one or more secondary services associated with the primary service (such as name, a medical code number such as a CPT code identifying the service according to the nomenclature used by a formal medical classification system, and a secondary procedure identifier that is used by application server 116 to uniquely identify the particular secondary service in association with the unique procedure identifier for the primary service), items of information describing one or more products associated with the primary service (such as name(s), a list of dosage level options for prescription drugs, size options for certain medical supplies, an indication of whether a prescription is required to purchase the product, and a bundled product identifier that is used by application server 116 to uniquely identify the particular product in association with the unique procedure identifier for the primary service), one or more procedure identifiers for other services for which an information record is maintained within available services database 114g that are considered to be secondary services associated with the primary service, one or more product identifiers for other products for which an information record is maintained within available products database 114i that are included in the bundled set with the primary service, an indication of whether each of the products included in the bundled set or performance of each of the one or more secondary services (for which a single customer payment for the bundled set will be disbursed among different respective providers for the services and/or products in the bundled set) is optional or required in association with performance of the primary service, and an indication of whether the primary service is required to be performed at an outside facility. In addition, in such embodiments, for each service for which the information record includes an indication that the service is offered as a primary service of a bundled set, the cost information that is included in the respective information record for the primary service that is maintained within available services database 114g can include respective cost information for each of the primary service and each of the one or secondary services, the one or more products, and, if required, the use of an outside facility for the primary service individually included in the bundled set (for example, average prices for each service, product, and facility of the bundled set for patients that are uninsured and/or have a high deductible insurance plan) in addition to an average price for purchasing the bundled set that is offered by providers registered with server system 110.

Service offer database 114h is used to maintain information records for healthcare services that are being offered by providers registered with the healthcare marketplace system 100 for purchase by customer users registered with the system. In this regard, it should be noted that the same service may be separately offered by multiple different providers registered with the system and, thus, service offer database 114h can include multiple information records for the same service that are each associated with a different provider. For each offered service for which a respective information record is maintained within service offer database 114h, various items of information relevant to the service being offered, such as the unique procedure identifier for the information record within available services database 114g for the service, the unique account identifier for the account information record (within physician profile database 114b, practice group profile database 114c, or hospital system profile database 114d) of the provider that is offering the service through the system, the unique physician account identifier for the account information record within physician profile database 114b of the physician user that will perform the service, a location at which the service will be performed, a discounted price for purchasing the service within marketplace system 100, a regular price for the service when the service is purchased outside of the system, the unique account identifier for the account information record (within physician profile database 114b, practice group profile database 114c, or hospital system profile database 114d) of the provider for which payment for the service when purchased through the system is to be directed, a compensation amount to be transferred to the provider for which payment for performing the service is to be directed, additional descriptive information that may be provided by the provider offering the service, a unique procedure offer identifier that is used by application server 116 to uniquely identify the offering of the particular service by the provider within the system, and any other suitable information may be included in the respective information record for the offered service that is maintained within service offer database 114h.

In exemplary embodiments, the system has associated the service offer with one or more healthcare products (for example, a drug that is commonly prescribed in association with the service being offered) and, for each healthcare product that is indicated as having been associated with the service offer, a discounted price for purchasing the particular product from the non-registered, affiliated pharmacy in association with a purchase of the service from the provider offering the particular service within the system, a regular price for purchasing the product from the non-registered, affiliated pharmacy, the unique account identifier for the account information record (within physician profile database 114b, practice group profile database 114c, or hospital system profile database 114d) of the provider for which payment for the product when purchased through the system in association with the service is to be directed, and a compensation amount to be transferred to the provider for which payment for purchasing the product is to be directed.

Additionally, in exemplary embodiments, the information records for offered services that are maintained within service offer database 114h can include information records that include additional information for services that are offered by providers registered with the system as a bundled set of services or one or more services and one or more products. For example, the items of information relevant to the bundled set included in the respective information record for an offered service within service offer database 114h that is indicated to be a primary service of a bundled set may further include, for example, an indication of whether the primary service is to be performed at an outside facility and, if the primary service is to be performed at an outside facility, items of information pertaining to each of one or more facilities that may be used to perform the primary service such as, for example, name, address, contact information, facility fee, and compensation information indicating a financial account that is used by the facility for receiving a facility fee.

Likewise, in another example, such items of information relevant to the bundled set included in the respective information record for an offered service within service offer database 114h that is indicated to be a primary service of a bundled set of services or one or more services and one or more products may also include, for example, if a prescription is required to purchase the product (for example, the physician user that would be performing the primary service), a compensation amount to be transferred to the provider for which payment for performing the secondary service is to be directed, and an indication of whether the product is optional or required in association with performance of the primary service.

Available products database 114i is used to maintain information records for various healthcare products (for example, prescription drugs and medical supplies) that can be offered by pharmacies registered with server system 110 (that is, pharmacies for which an account information record is maintained within pharmacy profile database 114e) for purchase by customer users registered with the system. For each product for which an information record is created, various items of information relevant to the product, such as name(s), a list of dosage level options (for prescription drugs), size options (for certain medical supplies), and the like, a description of the product, an indication of whether a prescription is required to purchase the product, information for rendering a respective predefined fillable form for submitting prescription information for the product within a user interface, cost information (for example, average prices for the product for patients that are uninsured and/or have a high deductible insurance plan and a lowest price for purchasing the product that is offered by pharmacies registered with server system 110. In exemplary embodiments, the respective information records for each particular product that is maintained in available products database 114i can further include a list of alternative, equivalent, and generic products for the particular product along with the unique product identifier for the respective information record that is maintained in available products database 114i for each of the alternative, equivalent, and generic products included in the list.

Product offer database 114j is used to maintain information records for offers of healthcare products that are being made by pharmacies registered with the system for purchase by customer users registered with the system. In this regard, it should be noted that the same product might be separately offered by multiple different pharmacies registered with the system.

Transaction information database 114k is used to maintain information records for purchases that have been made via the system by registered customer users of healthcare services and products being offered by registered providers. In general, the items of information relevant to each purchase that is included in the respective information record for the purchase that is maintained within the transaction information database 114k can include, for example, the unique customer account identifier of the account information record for the purchasing customer within customer profile database 114a.

For each purchase of a service that has been made using the system, the items of information relevant to the purchase included in the respective information record for the purchase that is maintained within transaction information database 114k may further include the unique physician account identifier for the account information record within physician profile database 114b of the physician user that is designated as performing the purchased service in the information record for the purchased service within service offer database 114*h*, an indication of whether the purchase has been redeemed and, if the purchase has been redeemed, a redemption date.

In exemplary embodiments, the user interface can be a web-based user interface, implemented as a web-based software application hosting a corresponding website that provides a number of web pages (that is, screens) to offer the services implemented by application server 116 to users. For example, a user can access the corresponding website using a web browser implemented within a client application 142 executing on a client system 140.

Figure 3A:
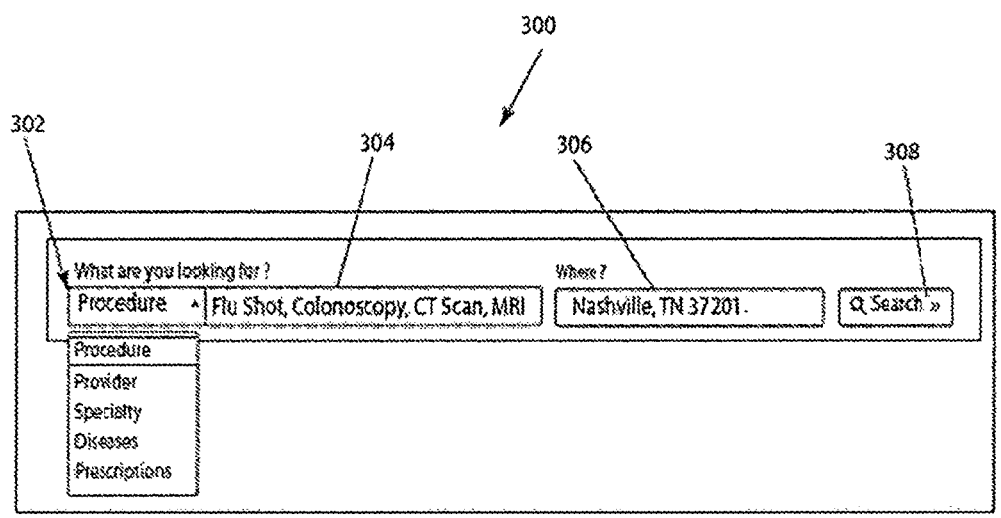

FIG. 3A is a screen shot illustrating an example of a graphical user interface provided by such a home page 300 for customer portal 120. In the illustrated example, the search interface provided at home page 300 could include a drop-down menu 302, a search entry field 304, a location entry field 306, and a search button 308. Drop-down menu 302 provides a set of selectable options that allow the user to search for particular procedures offered by provider users registered with the system, particular products offered by pharmacy users registered with the system, information on providers registered with the system, and information on health conditions that is maintained within system. In exemplary embodiments, navigation and search service 124 can be configured to use location information that may be gathered by any suitable location determining functionality implemented on the client system to provide a default location entry (for instance, city name and/or zip code) within location entry field 306. In such embodiments, navigation and search service 124 may be further configured to request permission from the user via the user interface to be able to access and utilize such location information for this purpose.

In one example, when the user selects the option within drop-down menu 302 to search for a particular service offered by provider users registered with the system, the user can then proceed to enter the name of the service within search entry field 304. In exemplary embodiments, navigation and search service 124 can be configured to, as the user enters the name of the service to be searched, identify and provide corresponding suggested entry completions in association with search entry field 304 (for instance, by comparing the entered characters with the various service names included in the respective information records for healthcare services that are maintained in available services database 114*g*). The user can then select one of the suggested entry completions at any point or continue to complete entry of the service name manually. In conjunction with selecting the particular service, the user can also enter a city name and/or zip code or opt to utilize a default location entry within location entry field 306 to localize a search radius for providers offering the selected service for purchase via marketplace system 100.

Navigation and search service 124 can conduct such a location-based search by accessing, for example, service offer database 114*h* in conjunction with physician profile database 114*b*, practice group profile database 114*c*, hospital system profile database 114*d*, and/or any other suitable information and databases to which the application server has access to filter the information records included within available services database 114*g* for healthcare services that match the specified search criteria, and then present the results of the search to user within a search result listing page.

Figure 3B:
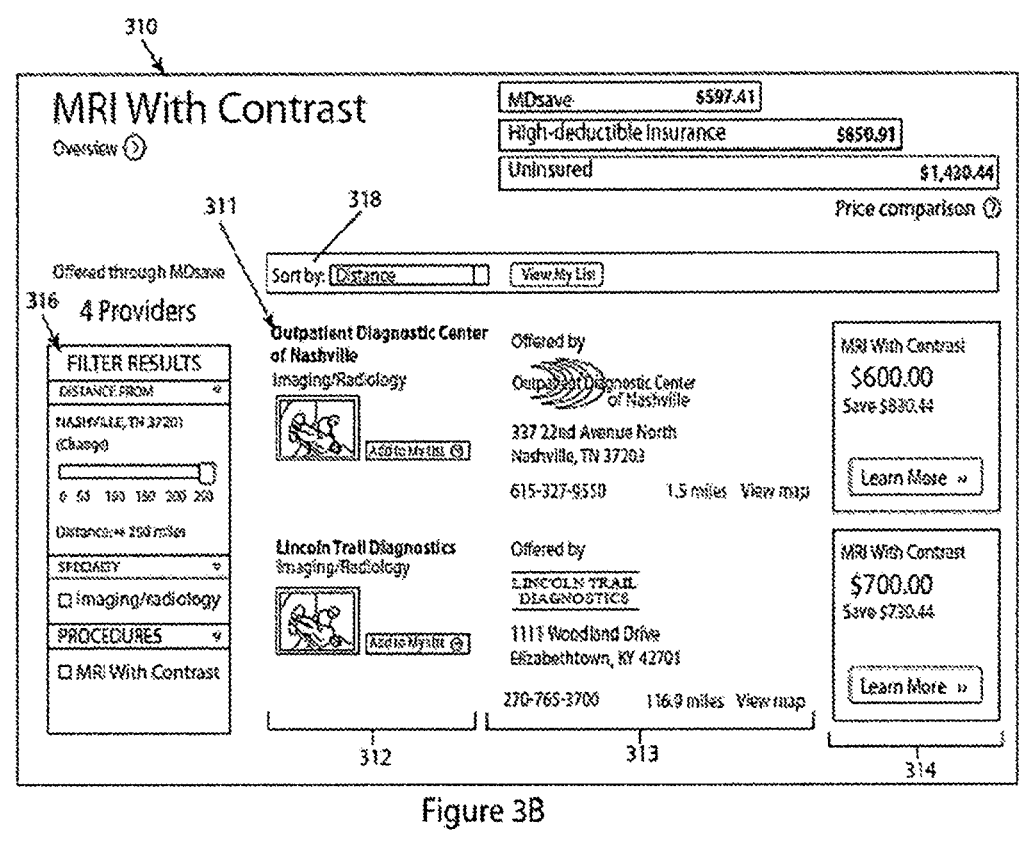

FIG. 3B is a screen shot illustrating an example of a GUI provided by a search result listing page 310 for customer portal 120 that presents a list of providers offering the service specified within search entry field 304 within a default search radius (for example, 50 miles) of the location specified within location entry field 306 returned in the search conducted by navigation and search service 124. In the illustrated example, search result listing page 310 includes a result listing section 311, a result filtering section 316, and a result sorting section 318. Result listing section 311 presents an entry for each offered service for which a respective information record is maintained within service offer database 114*h* that matches the specified search criteria. Result filtering section 316 provides various user interface controls for refining the results of the search presented within result listing section 311 by modifying the search criteria or inputting additional search criteria. In the illustrated example, result filtering section 316 includes a distance slide bar that is accessible to the user to increase or decrease the geographical search radius of searched providers offering the service specified within search entry field 302 and an option to refine the results according to one or more particular specialties of the physician that will perform the service. Result sorting section 318 provides user interface controls that can be accessed by a user to direct navigation and search service 124 to order the list of entries for offered services within result listing section 311 according to a specified criteria (for example, according to the price for purchasing the offered service via server system 110 or the distance between the location of the offered service and the location specified within location entry field 306). In exemplary embodiments, such a search result listing page 310 can be implemented to present any other appropriate information relevant to the search criteria specified by the user, such as, for example, a graphic depicting the average cost information included in the information record for the service specified in the search criteria that is maintained in available services database 114*g*.

In the example screen shot depicted in FIG. 3B, each entry for an offered service listed in result listing section 311 includes a first portion 312 presenting information from the account information record within physician profile database 114*b* of the physician that will perform the service as specified in the information record for the offered service within service offer database 114*h* (for example, the physician's name, specialty, and profile picture), a second portion 313 presenting information from the account information record of the provider that is offering the service through the system (for example, the name of the provider) and the location at which the offered service will be performed (for example, address and telephone number), and a third portion 314 presenting cost information for purchasing the offered service through application server 116 (for example, the discounted price for the service that is specified in the information record for the offered service within service offer database 114*h* and a cost savings difference between the discounted price and the regular price for the service when the service is purchased outside of the system from the provider as specified in the information record for the offered service within service offer database 114*h*), and an option to select to purchase the offered service listed in the entry (for example, via an "Add to Cart" button included within third portion 314).

As will be described in greater detail below, upon selecting one or more services and/or products for purchase in association with a session with application server 116, the user will then have an option to navigate to a customer purchase page (for example, a "Check-Out" page) to proceed with purchasing the selected item(s) with respect to an account information record maintained within customer profile database 114a for a registered customer user.

Additionally, for each entry for an offered service listed in result listing section 311, first portion 312 can further include a hyperlink or other reference that is accessible by the user via the user interface to navigate to a physician profile page that presents information regarding the physician that will perform the offered service (an example of such a physician profile page will be described below with reference to FIG. 3D). Referring again to example home page 300 illustrated in FIG. 3A, in another example in which the user selects the option within drop-down menu 302 to search for a particular product offered by pharmacies registered with the system, the user can then proceed to enter the name of the particular product within search entry field 304.

Referring again to example home page 300 illustrated in FIG. 3A, in another example in which the user selects the option within drop-down menu 302 to search for information on health conditions maintained within server system 110, the user can then proceed to enter the name of a particular health condition within search entry field 304. In exemplary embodiments, navigation and search service 124 can be configured to, as the user enters the name of the condition to be searched, identify and provide corresponding suggested entry completions in association with search entry field 304 (for instance, by comparing the entered characters with the various condition names included in the respective information records for conditions that are maintained in condition information database 114.+-.). The user can then select one of the suggested entry completions at any point or continue to complete entry of the condition name manually. For example, upon the user selecting the search button, navigation and search service 124 can be configured to provide a list of suggested condition names that are determined to be similar to the text entered in search entry field 304 from which the user can select upon making a determination that the text entered in search entry field 304 does not more closely correspond to a particular condition for which a corresponding information record is maintained in condition information database 114f.

The condition information page for a particular condition can be implemented to present a set of appropriate information relevant to condition based on the information that is maintained in the respective information record for the condition that is maintained in condition information database 114f such as, for example, name, description, causes, risk factors, symptoms, and common treatments. In exemplary embodiments, the condition information page for a particular condition can be implemented to provide a list of corresponding healthcare services that can be offered by providers registered with server system 110 in conjunction with a respective hyperlink (or other reference) for each corresponding service that is accessible by the user within the user interface to navigate to a healthcare service information page that presents information regarding the specified service.

Referring now to FIG. 3C, a screen shot illustrating an example of a GUI provided by a healthcare service information page 320 implemented by navigation and search service 124 for a particular healthcare service is provided. In the illustrated example, healthcare service information page 320 includes a procedure overview section 322, a cost comparison graphic 324, and a provider listing section 326. The information presented in procedure overview section 322 can be generated based on the procedure detail information included in the respective information record that is maintained for the particular service in available services database 114g. Likewise, information that is presented in cost comparison graphic 324 can be generated based on the average cost information included in the respective information record that is maintained for the particular service in available services database 114g (for example, to present a display of average prices for the service for patients that are uninsured and/or have a high deductible insurance plan in comparison with an average price for purchasing the service through offers from providers registered with server system 110).

As noted above, for a particular healthcare service that is being offered as a bundled set of services or one or more services and one or more products, the cost information that is included in the respective information record for the primary service that is maintained within available services database 114g can include respective cost information for each of the primary service, one or more secondary services and/or one or more products included in the bundled set, and, if required, the use of an outside facility for the primary service individually. In this regard, the information that is presented in cost comparison graphic 324 for such a bundled set can be generated to present a display of the aggregate sum of the respective individual prices for each of the primary service, the one or more secondary services and/or one or more products included in the bundled set.

In the present example, provider listing section 326 further includes a location entry field 327 that, in conjunction with a "submit" button 328, allows a user to specify a particular location (for example, a city name and/or zip code) and submit a request for navigation and search service 124 to conduct a search and update the information presented in provider listing section 326 to present a list of providers offering the particular service within the default search radius of the newly specified location. Navigation and search service 124 can also be configured to, in response to such a request, update the location that is maintained within the session data object for the session with application server 116 that is presently being maintained for the user.

Figure 3D:

Additionally, a screen shot illustrating an example of a GUI provided by a physician profile page 330 implemented by navigation and search service 124 for a particular physician user registered with server system 110 is provided in FIG. 3D.

In the illustrated example, physician profile page 330 includes a physician information section 332 and an offered procedures section 336. The information presented in physician information section 332 can be generated based on the information that is included in the respective account information record that is maintained for the particular physician user in physician profile database 114b and may include various items of information relevant to the physician, such as name, practice specialty, office location(s) and hours, a profile picture, contact information, biographical information (such as awards, honors, publications, patient testimonials, and other information that may be of interest to prospective customers accessing the system), URLs or references to websites and social media profiles, and group practice, hospital, and pharmacy affiliation(s).

In exemplary embodiments, as further illustrated in FIG. 3D, physician information section 332 can further include additional user interface elements such as a "Leave a review" button 333, a "Request an appointment" button 334, and a map element 335 depicting a mapped location of an office location included within respective account information record that is maintained for the particular physician user in physician profile database 114*b* (which navigation and search service 124 may be configured to generate by remotely accessing a third-party mapping service). In response to a user selecting "Leave a review" button 333, navigation and search service 124 can be configured to implement suitable user interface controls for allowing the user to post or submit a review of the particular physician to server system 110. In response to receiving such a review, navigation and search service 124 can be configured to, for example, include information pertaining to the review within the respective account information record that is maintained for the particular physician user in physician profile database 114*b* or send an electronic message to the physician user pertaining to the review, for example, by way of email utilizing the contact information specified in the respective account information record for the physician.

In response to a user selecting "Request an appointment" button 334, navigation and search service 124 can be configured to implement suitable user interface controls for allowing the user to submit a request for scheduling an appointment to the particular physician user (for example, by sending a notification to the physician user by utilizing the contact information specified in the respective account information record for the physician that includes contact information for the user). Navigation and search service 124 may also be configured to implement suitable user interface controls for allowing the user to schedule an appointment with the particular physician user. Navigation and search service 124 may provide this functionality by, for example, accessing an appointment scheduling service with which the particular physician user is associated, which may be a service offered by application server 116 or offered by a third-party service provider.

In the present example, as illustrated in FIG. 3D, the information presented in offered procedures section 336 of physician profile page 330 can include a listing of healthcare services offered by the particular physician for purchase through marketplace system 100. More specifically, offered procedures section 336 presents an entry for each offered service for which a respective information record is maintained within service offer database 114*h*.

In exemplary embodiments, each entry for an offered service listed in offered procedures section 336 for which the respective information record for the offered service within service offer database 114*h* includes an indication that the provider offering the service through the system has associated the service offer with one or more healthcare products.

Referring again to example home page 300 illustrated in FIG. 3A, in another example in which the user selects the option within drop-down menu 302 to search for providers registered with the system, the user can then proceed to enter the name of a particular provider within search entry field 304. The respective practice group profile page for the corresponding practice group may further include a listing of healthcare services offered by the particular practice group for purchase through marketplace system 100 that presents an entry for each offered service for which a respective information record is maintained within service offer database 114*h* that identifies, as the provider that is offering the service through the system. The respective hospital system profile page for the corresponding hospital system may further include a listing of healthcare services offered by the particular hospital system for purchase through marketplace system 100 that presents an entry for each offered service for which a respective information record is maintained within service offer database 114*h* that identifies, as the provider that is offering the service through the system, the unique account identifier for the account information record within hospital system profile database 114*d* of the particular hospital system.

Alternatively, when a user selects the option within drop-down menu 302 to search for providers registered with the system, the user, rather than searching for a specific provider by name, conducts a search for local providers by entering a city name and/or zip code or opt to utilize a default location entry within location entry field 306 to localize a search radius. Navigation and search service 124 can conduct such a location-based search by accessing physician profile database 114*b*, practice group profile database 114*c*, and hospital system profile database 114*d* to filter the account information records for providers maintained by database server 112 for local providers, and then present the results of the search to user within a provider search result listing page.

Similarly, and referring again to FIG. 3A, when a user selects the option within drop-down menu 302 to conduct a search with respect to a particular specialty, the user can then proceed to enter the name of a particular practice specialty within search entry field 304. In exemplary embodiments, navigation and search service 124 can be configured to provide a drop-down within search entry field 304 that allows the user to select one of a plurality of specialties recognized by server system 110.

The payment information input by the user may be an instruction to use the billing information included within the respective account information record established for the user within customer profile database 114*a* or submission of an alternative payment information such as, for example, bank account information, credit or debit card information, or other electronic payment information (such as information for utilizing an account the user has with PayPal or any another entity facilitating payments and money transfers to be made through the Internet), which may be for an account maintained for the user or an account maintained for another person or entity that the user is authorized to utilize for this purpose. Account management service 122 can be configured to, upon the authorization and appropriate payment information being provided by the user, access a corresponding third-party payment servicing system and utilize the payment information to direct the payment servicing system to transfer the amount for the payment authorized by the user from the account servicer of the user to a financial account maintained by the providers of marketplace system 100. In this regard, the respective account information record established for the user within customer profile database 114*a* can further include an account status that is managed by account management service 122 for the user indicating whether the user is presently provided with the ability to make prepaid purchases of healthcare services and products offered within marketplace system 100.

Purchasing service 126 may be configured, for example, to implement a user interface that includes one or more pages with user interface controls accessible by the user to guide the user through the purchasing process and prompt the user to input and make selections of various types of information. For example, a purchase information section may be included within a payment page provided within the user interface that includes a respective entry for each offered item indicated as having been selected by the user in the session data object. For each offered product for which a respective entry is included in the purchase information section, the entry may include, for example, information retrieved from pharmacy profile database 114*e*, available products database 114*i*, product offer database 114*j*, service offer database 114*h* and the session data object such as pharmacy name, product name along with any dosage level, form of the medicine, and quantity for a prescription drug or size option for a medical supply, and an indication of whether a prescription is required to purchase the product.

The purchase information section included within the user interface implemented for the payment page may further include a total price for the purchase that is equal to a sum of the respective price for purchasing the corresponding offered item included for each entry included in the purchasing information section. In exemplary embodiments, purchasing service 126 may be configured to adjust the total price based on any applicable state taxes or any discount codes submitted by the user. In this regard, purchasing service 126 may be further implemented to provide a user interface element allowing a user to submit any application discount codes to application server 116.

Upon the user reviewing the information provided in the purchase information section and making any desired modifications and selections via the user interface controls implemented within the payment page, the user may then proceed to access further user interface controls implemented within a payment section of the payment page to make a prepaid purchase of the one or more offered items for which respective entries are included in the purchase information section in a single transaction with purchasing service 126 by submitting customer purchase information specifying a funding source to use for purchasing the one or more offered items and providing an authorization for server system 110 to issue a request to the funding source for funds in the amount of the total price for the purchase listed in the purchase information section.

Purchasing service 126 can be further configured to credit or otherwise direct a disbursement of funds to be made to, if the product offer being purchased is offered through a pharmacy registered with server system 110, the financial account specified by the compensation information included in the account information record within pharmacy profile database 114*e* of the pharmacy that is offering the product with the corresponding payment amount that is specified to be transferred to the pharmacy indicated by the respective information record in product offer database 114*j* for the offered product. Upon receiving reimbursement for the invoiced amount from the funding source, a financial account maintained by the providers of marketplace system 100 can be credited with any negotiated or contracted commission fee for offering the product for purchase via the system (which may be, for example, a fixed percentage of the payment amount and/or a flat fee).

For processing payment for each offered product that is being offered through a pharmacy registered within server system 110 for which a prescription is required for the purchase, purchasing service 126 may be configured to navigate the user interface to a prescription submission page prior to processing the payment for the offered prescription product. Prescription submission page can be implemented by purchasing service 126 to provide user interface controls for allowing the user to submit the required prescription information for purchasing the offered product. The plurality of options for submitting prescription may include, for example, emailing an image of a prescription document to an email address for an account maintained in association with server system 110 for such a purpose, faxing a copy of a prescription document to a fax number utilized in association with server system 110 for such a purpose, uploading a copy of a prescription document to application server 116, completing information fields of a respective predefined fillable form for generating a prescription document for the particular product within the user interface, and indicating that the prescription will be submitted by the customer user or a physician user at a later time to a pharmacy.

Upon receiving the prescription document, the pharmacy can perform a verification of the prescription document, for example, by contacting the medical specialist listed as having prescribed the product.

Figure 4A:
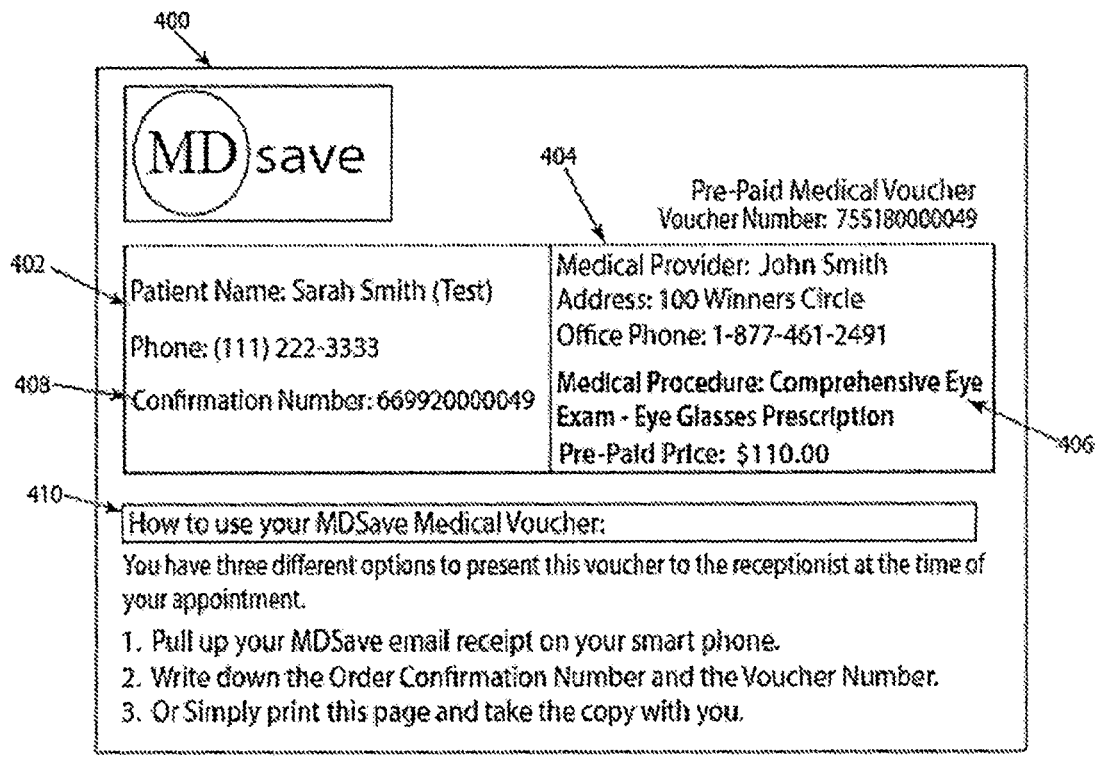
FIG. 4A is an illustration of an example voucher that may be generated within a user interface by functions provided within a customer portal for a purchased service in accordance with exemplary embodiments of the present invention.

Purchasing service 126 can also be configured to, upon processing the payment for the purchase of the offered service, generate a voucher for the customer user within the user interface for the purchased service utilized by the customer user to redeem the purchase and receive the service from the physician specified for the offered service (the providers of marketplace system 100 can have pre-arranged agreements with providers registered with the system that the providers will agree to honor such vouchers generated by purchasing service 126 for purchased services). An example of such a voucher is illustrated in FIG. 4A. As depicted in the example, example voucher 400 can be generated to include identifying information for the customer user 402, identifying and contact information for the physician specified for the offered service 404, a description of the purchased service 406, a confirmation number 408 for the purchase, which may be generated by purchasing service 126 based on the unique transaction identifier that is included in the respective information record for the purchase that is maintained within transaction information database 114*k*, and instructions for redeeming the voucher 410. The confirmation number may also be provided in the electronic confirmation message to the customer user and electronic notifications to the physician user that will be performing the service and the provider user for the offered service sent by purchasing system 126 to the customer user. The voucher can be presented to the user within the user interface, for example, as printable and/or machine-readable form.

Similarly, for processing payment for each offered service that is being offered as a primary service in conjunction with a bundled set of services or one or more services and one or more products, purchasing service 126 may be configured to utilize the purchase information provided by the user to issue a request for the portion of the total purchase price authorized by the user that is allocated for the offered service to the funding source specified in the purchase information. In contrast to the processing performed by purchasing service 126 for offered services or offered products that are not being offered in conjunction with a bundled set, however, a respective sub-portion of the payment amount for the offered service is held separately with respect to the primary service, each secondary service, each bundled product, and any facility specified for the purchased offered service.

Purchasing service 126 can be configured to, upon processing the payment for the purchase of the offered service that is being offered as a primary service in conjunction with a bundled set, navigate the user interface to a purchase confirmation page and send an electronic confirmation message to the customer user and electronic notifications to the each physician that will perform a service of the bundled set, each pharmacy from which a purchased product is offered within the bundled set, Purchasing service 126 can be also be configured to generate a respective information record for the completed purchase with corresponding information within transaction information database 114*k*, which initially indicates that the purchase has not yet been redeemed with respect to the primary service.

Figure 4B:
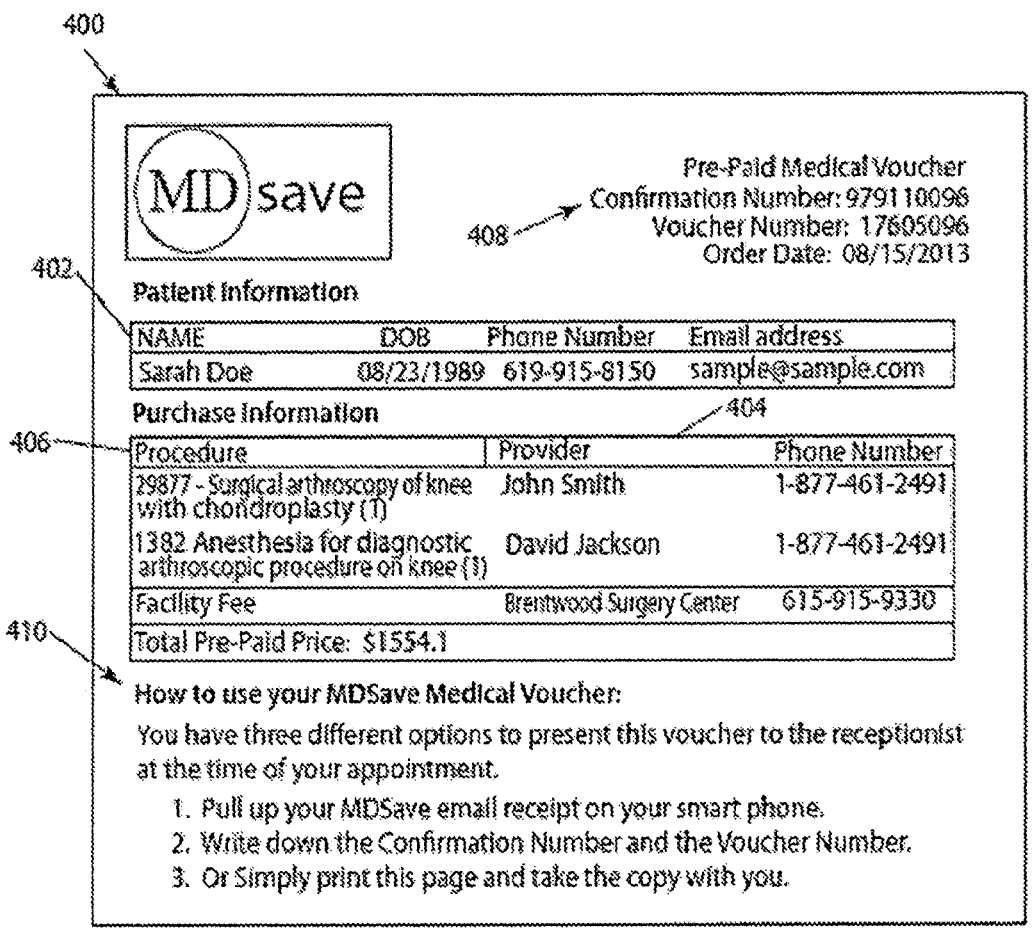
FIG. 4B is an illustration of an example voucher that may be generated within a user interface by functions provided within a customer portal for a purchased service that is offered as a bundled set in accordance with exemplary embodiments of the present invention.

Purchasing service 126 can also be configured to, upon processing the payment for the purchase of the offered service that is being offered as a primary service in conjunction with a bundled set, generate a voucher for the customer user within the user interface for the purchased service that can be utilized by the customer user to redeem the purchase and thereby receive the service from the corresponding physician specified for each of the services of the bundled set and receive the product from the corresponding pharmacy specified for each of the products of the bundled set (the providers of marketplace system 100 can have pre-arranged agreements with providers registered with the system that the providers will agree to honor such vouchers generated by purchasing service 126 for purchased services and products). An example of such a voucher that is generated for a purchase of a bundled set is illustrated in FIG. 4B. As depicted in the example, example voucher 400 can be generated to include identifying information for the customer user 402, identifying and contact information for each physician specified for a service, each pharmacy specified for a product, and any facility included in the offered service 404, a description of each service and product of the purchased service 406, a confirmation number 408 for the purchase, which may be generated by purchasing service 126 based on the unique transaction identifier that is included in the respective information record for the purchase that is maintained within transaction information database 114k, and instructions for redeeming the voucher 410. The confirmation number (or any other suitable redemption information such as a one or two dimensional bar code, a QR code, or any other form of machine readable information) may also be provided in the electronic confirmation message to the customer user and electronic notifications to each physician user that will be performing a service, each pharmacy that will be providing a product, and the provider user for the offered service sent by purchasing service 126 to the customer user. The voucher can be presented to the user within the user interface, for example, as printable and/or machine-readable form. In exemplary embodiments, for each purchased product included in the bundled set for which a prescription is required to purchase the product, the redemption information included in the voucher for receiving the product from the corresponding pharmacy specified for the product may not become valid until a notification of any necessary submission and verification of the prescription document has been received by purchasing service 126.

For example, such a profile management interface may be implemented to allow the customer user to manage personal information, view a history of purchase transactions performed by the user within server system 110 (and relevant information for each purchase including voucher redemption status), submit any required prescriptions for purchases of offered products that have been made, manage and review any continuing prescriptions, and print vouchers generated for services and products purchased and otherwise access voucher redemption information.

Upon the user indicating an intention to register as a physician user, the user will be able to initiate a registration session with account management service 131 to register a physician account with server system 110. The user interface may also be implemented by account management service 131 to prompt the user to specify any affiliated pharmacies or for any group practice or hospital affiliation codes. In this regard, account management service 131 may be implemented to provide user interface controls allowing the user to search for pharmacies registered with server system 110 (for example, by name), access pharmacy profile database 114e to locate account information records for pharmacies matching the search criteria, and provide user interface controls allowing the user to register an affiliation within server system 110 with any pharmacy returned in the search.

Account management service 131 can be configured to access database server 112 to create the respective account information record for the user within physician profile database 114b based on the information input by the user during the registration process. In exemplary embodiments, the user interface implemented by account management service 131 may be further configured to provide user interface controls for requesting authorization for payment of a predetermined fee to gain access to the ability to offer healthcare services for purchase within marketplace system 100. Such a fee may be, for example, a one-time charge or a periodic charge (such as a monthly, biannual, or annual fee).

Upon the user indicating an intention to offer a healthcare service for purchase (for example, by selecting a "Offer Service" tab within the physician account page implemented by provider portal 130), the user will be able to initiate a service offering with procedure management service 133 to offer a healthcare service for purchase via server system 110. For example, the user may be provided with a drop-down menu providing a list of selectable medical specialties and, upon selecting a particular medical specialty, the user can be presented with a list of selectable healthcare services for which an information record for the service is maintained within available services database 114g in association with the specialty.

As discussed above, when a payment for an offered service is processed by purchasing service 126, a financial account maintained by the providers of marketplace system 100 holds the payment amount to be transferred to the provider for which payment for the service is to be directed until an indication is received that the purchased service has been performed by the physician that is specified in service offer database 114h for performing the service. Purchasing service 126 can also be a voucher for the customer user to use with respect to the purchased service to redeem the purchase by receiving the service from the physician specified for each service included in the purchase. Such a voucher can include a confirmation number or other redemption code for the purchase.

Upon the user indicating an intention to request payment for a purchased service that has been performed (for example, by selecting a "Voucher Processing" tab within the physician account page implemented by provider portal 130), the user will be able to initiate a voucher processing session with transaction processing service 136. In particular, transaction processing service 136 may be configured, for example, to implement a voucher history page within the user interface that presents information relevant to the physician user for a list of purchases for which the respective information record for the purchase that is maintained within transaction information database 114k includes the unique physician account identifier for the physician user within physician profile database 114b as the physician user that is designated as performing a service included the purchase (for example, a primary or secondary service for a bundled set of services or one or more services and one or more products). The relevant information for each listed purchase may include, for example, the voucher confirmation number or redemption code, name and contact information for the customer user, a description of the service the physician user is designated as performing for the purchase, a purchase date, and a voucher redemption status. Such a voucher history page may also be accessed in association with the user account for the physician user to verify vouchers presented by customers requesting to have a service performed in association with a voucher.

The voucher history page can also provide a user interface element in association with each of the listed purchases for which the voucher redemption status for the service the physician user is designated as performing indicates the service has not been performed that is accessible by the physician user to submit a verification to application server 116 that the physician user has performed the service for the customer user in accordance with the purchase. Transaction processing service 136 can be configured to, upon such a verification being submitted, initiate a transfer of the payment amount specified for the service performed by the physician user in service offer database 114h and held in the financial account maintained by the providers of marketplace system 100 to the financial account listed for receiving the payment amount for service that is specified in service offer database 114h. Additionally, if the service performed by the physician is a primary service of a bundled set for which a particular outside facility that has been selected for performing the primary service, transaction processing service 136 can be configured to initiate a transfer or otherwise direct a disbursement of the facility fee specified for the service performed by the physician user in service offer database 114h and held in the financial account maintained by the providers of marketplace system 100 to the financial account for the facility that is indicated by the compensation information for the facility.

In exemplary embodiments, transaction processing service 136 can further be configured to, for each purchase of an offered product for which a prescription is required for the purchase that is being offered through a pharmacy registered within server system 110 or a pharmacy that is not registered with the system but affiliated with the physician, and for which the respective information record in transaction information database 114k for the purchase indicates that the physician user will be writing the prescription or otherwise providing an offered service purchased through the system with which the purchase of the offered product is associated, allow the physician user to navigate the user interface to a prescription submission page that is implemented to provide user interface controls for allowing the physician user to submit the required prescription information for purchasing the offered product on behalf of the purchasing customer user (for example, by selecting a "Prescription Submission" tab within the physician account page implemented by provider portal 130).

Likewise, account management service 131 may be implemented to provide user interface controls allowing the user to search for pharmacies registered with server system 110 (for example, by name), access pharmacy profile database 114e to locate account information records for pharmacies matching the search criteria, and provide user interface controls allowing the user to register an affiliation within server system 110 with any pharmacy returned in the search.

In exemplary embodiments, the user interface implemented by account management service 131 may be further configured to provide user interface controls for requesting authorization for payment of a predetermined fee to gain access to the ability to offer healthcare services for purchase within marketplace system 100. Such a fee may be, for example, a one-time charge or a periodic charge (such as a monthly, biannual, or annual fee). The fee may also be assessed for each new physician account registered with server system 110 by the user as an affiliated physician of the practice group. Alternatively, the user interface implemented by account management service 131 may be configured to provide user interface controls for receiving an activation code to gain access to the ability to offer healthcare services for purchase within marketplace system 100 or may be configured to provide such access to the user (and/or any new physician accounts registered for affiliated physicians by the user with server system 110) in response to receiving a particular group or hospital affiliation code from the user. Upon a user registering a practice group account with server system 110 to establish an account information record within practice group profile database 114c and logging into his or her practice group account (for example, by accessing a login user interface element or a login screen within the user interface implemented by navigation and search service 124 to provide the user name and password associated with the account), the user may be directed to a practice group account page implemented by provider portal 130 that provides a set of user interface controls that can be accessed by the user to access functionality provided by procedure management service 133 to offer healthcare services performed by affiliated physicians for purchase by customer users registered with the system, functionality provided by transaction processing service 136 to request payment for purchased services that have been performed, and to access various account management functions provided by account management service 131.

For example, the user may be provided with a drop-down menu providing a list of selectable medical specialties and, upon selecting a particular medical specialty, the user can be presented with a list of selectable healthcare services for which an information record for the service is maintained within available services database 114g in association with the specialty.

In exemplary embodiments, procedure management service 133 can be further configured to assist the user with offering one or more healthcare products for purchase in association with the offered service for purchase and further populate the respective information record for the offered service within service offer database 114h. In exemplary embodiments, procedure management service 133 can also assist the practice group administrator with offering services for purchase as a bundled set of services or one or more services and one or more products within marketplace system 100 and establishing the respective information record for the service offered as a bundled set within service offer database 114h.

For a selected service for which such an indication is provided, procedure management service 133 may be configured, for example, to implement user interface controls accessible by the user to guide the user through the process for offering the selected service as a primary service of a bundled set and prompt the user to input various types of information to populate a respective information record that is established in association with the unique practice group account identifier for the practice group within service offer database 114h. Upon the user indicating an intention to request payment for a purchased service that have been performed (for example, by selecting a "Voucher Processing" tab within the practice group account page implemented by provider portal 130), the user will be able to initiate a voucher processing session with transaction processing service 136. The user interface may also be implemented by account management service 131 to prompt the user to specify affiliated physician users and enter any practice group affiliation codes.

In exemplary embodiments, the user interface implemented by account management service 131 may be further configured to provide user interface controls for requesting authorization for payment of a predetermined fee to gain access to the ability to offer healthcare services for purchase within marketplace system 100. Such a fee may be, for example, a one-time charge or a periodic charge (such as a monthly, biannual, or annual fee). In exemplary embodiments, healthcare marketplace system 100 may be further implemented to provide an interactive pricing tool 137 for use by healthcare service providers in setting prices for healthcare services being offered to prospective patients through the system, including bundled sets of services for which the network-based application facilitates a disbursed distribution of the payment among multiple service providers that perform services (or provide use of a health care facility for performing a service) included in a bundled set of services. Exemplary embodiments can thereby assist in reducing the amount of overhead necessary to establish and monitor a well-developed and maintained fee schedule that is market sensitive, fiscally responsible, and organizationally sound, particularly for bundled payment arrangements for services that are delivered by two or more providers during a single episode of care for a patient.

Figure 5:
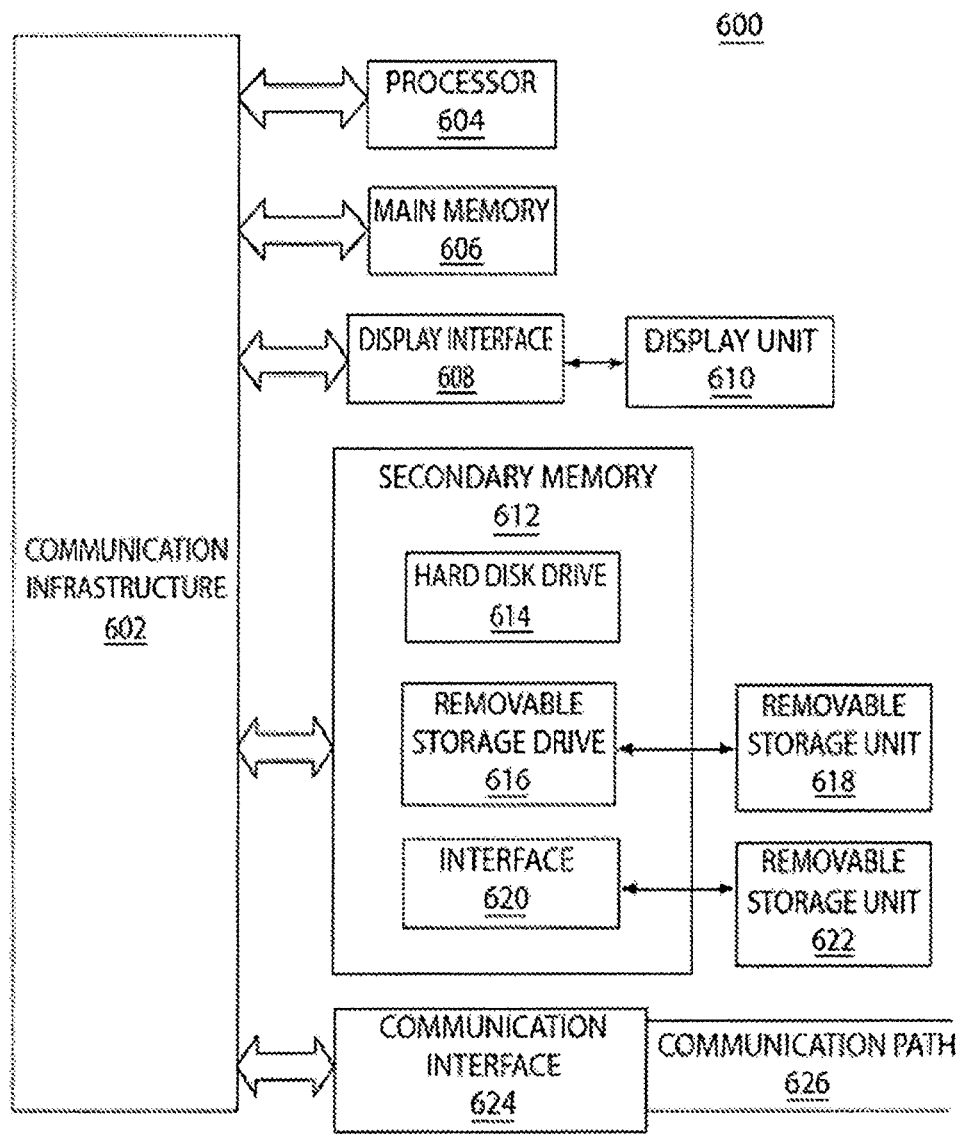
FIG. 5 is a block diagram of an exemplary computer system 600 that can be used for implementing exemplary embodiments of the present invention.

FIG. 5 is a block diagram of an exemplary computer system 600 that can be used for implementing exemplary embodiments of the present invention. Computer system 600 includes one or more processors, such as processor 604. Processor 604 is connected to a communication infrastructure 602 (for example, a communications bus, cross-over bar, or network). Various software embodiments are described in terms of this exemplary computer system. After reading this description, it will become apparent to a person of ordinary skill in the relevant art(s) how to implement the invention using other computer systems and/or computer architectures.

Exemplary computer system 600 can include a display interface 608 that forwards graphics, text, and other data from the communication infrastructure 602 (or from a frame buffer not shown) for display on a display unit 610. Computer system 600 also includes a main memory 606, which can be random access memory (RAM), and may also include a secondary memory 612. Secondary memory 612 may include, for example, a hard disk drive 614 and/or a removable storage drive 616, representing a floppy disk drive, a magnetic tape drive, an optical disk drive, etc. Removable storage drive 616 reads from and/or writes to a removable storage unit 618 in a manner well known to those having ordinary skill in the art. Removable storage unit 618, represents, for example, a floppy disk, magnetic tape, optical disk, etc. which is read by and written to by removable storage drive 616. As will be appreciated, removable storage unit 618 includes a computer usable storage medium having stored therein computer software and/or data.

In exemplary embodiments, secondary memory 612 may include other similar means for allowing computer programs or other instructions to be loaded into the computer system. Such means may include, for example, a removable storage unit 622 and an interface 620. Examples of such may include a program cartridge and cartridge interface (such as that found in video game devices), a removable memory chip (such as an EPROM, or PROM) and associated socket, and other removable storage units 622 and interfaces 620 which allow software and data to be transferred from the removable storage unit 622 to computer system 600.

Computer system 600 may also include a communications interface 624. Communications interface 624 allows software and data to be transferred between the computer system and external devices. Examples of communications interface 624 may include a modem, a network interface (such as an Ethernet card), a communications port, a PCM-CIA slot and card, etc. Software and data transferred via communications interface 624 are in the form of signals which may be, for example, electronic, electromagnetic, optical, or other signals capable of being received by communications interface 624. These signals are provided to communications interface 624 via a communications path (that is, channel) 626. Channel 626 carries signals and may be implemented using wire or cable, fiber optics, a phone line, a cellular phone link, an RF link, and/or other communications channels.

In this document, the terms "computer program medium," "computer usable medium," and "computer readable medium" are used to generally refer to media such as main memory 606 and secondary memory 612, removable storage drive 616, a hard disk installed in hard disk drive 614, and signals. These computer program products are means for providing software to the computer system. The computer readable medium allows the computer system to read data, instructions, messages or message packets, and other computer readable information from the computer readable medium. The computer readable medium, for example, may include non-volatile memory, such as Floppy, ROM, Flash memory, Disk drive memory, CD-ROM, and other permanent storage. It can be used, for example, to transport information, such as data and computer instructions, between computer systems. Furthermore, the computer readable medium may comprise computer readable information in a transitory state medium such as a network link and/or a network interface including a wired network or a wireless network that allow a computer to read such computer readable information.

Computer programs (also called computer control logic) are stored in main memory 606 and/or secondary memory 612. Computer programs may also be received via communications interface 624. Such computer programs, when executed, can enable the computer system to perform the features of exemplary embodiments of the present invention as discussed herein. In particular, the computer programs, when executed, enable processor 604 to perform the features of computer system 600. Accordingly, such computer programs represent controllers of the computer system.

Figure 6:
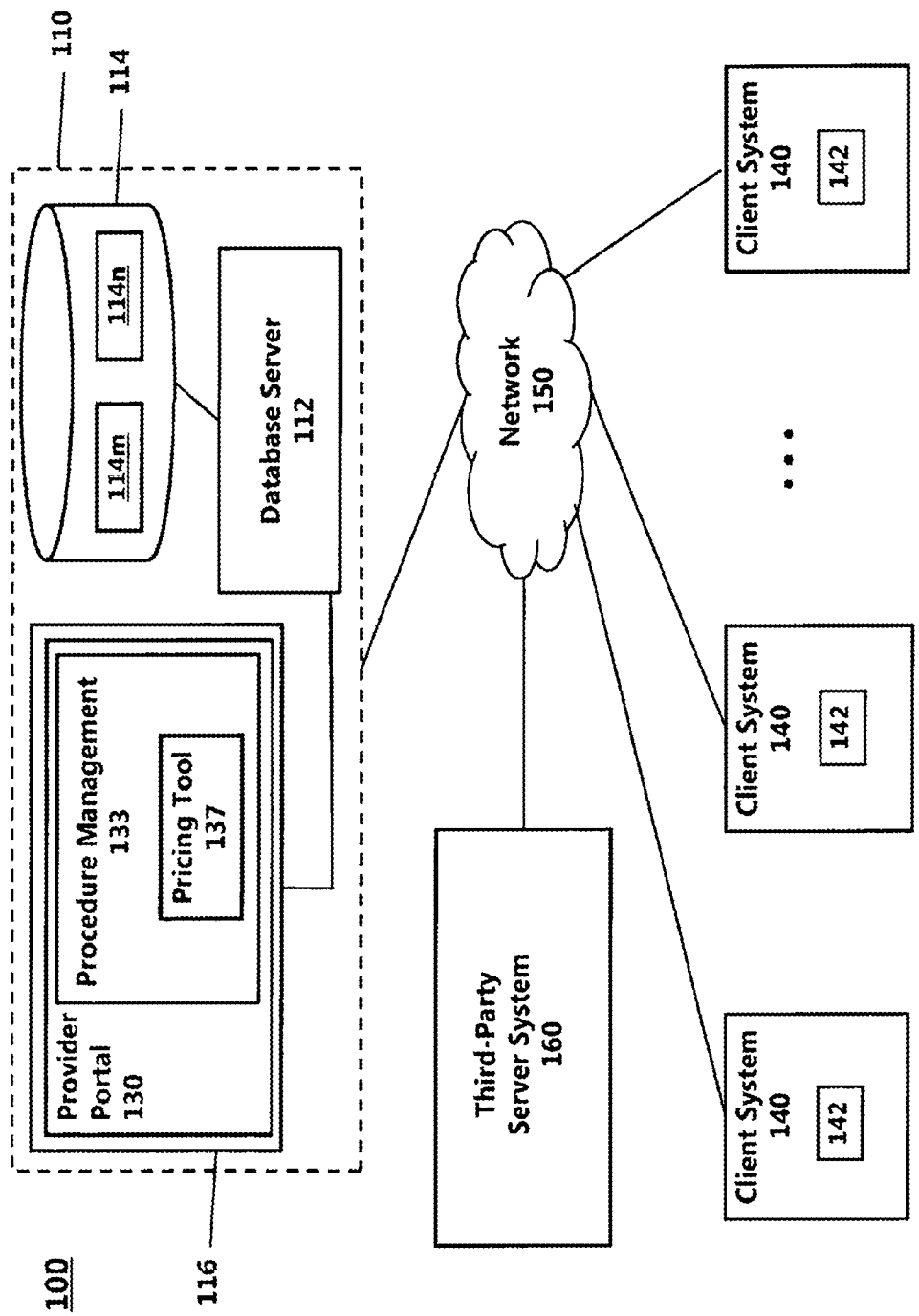
FIG. 6 is a schematic diagram illustrating a second example network architecture for a healthcare marketplace system that can be configured to implement exemplary embodiments of the present invention.

Referring now to FIG. 6, a schematic diagram illustrating example network architecture for healthcare marketplace system 100 within which an exemplary embodiment of a provider pricing tool 137 in accordance with the present invention is implemented. It should of course be understood that FIG. 6 is intended as an example, not as an architectural limitation for different embodiments of the present invention, and therefore, the particular elements depicted in FIG. 6 should not be considered limiting with regard to the environments within which exemplary embodiments of the present invention may be implemented.

In the example illustrated in FIG. 6, the particular components that are utilized for providing the provider pricing tool 137 are integrated within system 100 in conjunction with the components of the system as described above with reference to the exemplary embodiments illustrated FIGS. 1 and 2. More specifically, the pricing tool 137 is shown in FIG. 6 as being implemented within procedure management service 133 included within provider portal 130, and data store 114 further comprises a service pricing information database 114*m* and a cost adjustment information database 114*n* that are maintained by database server 112, are accessed by application server 116 via database services provided at a front end by database server 112, and retain information collected from a variety of data sources that is utilized in providing the services offered via the provider pricing tool 137 within the network service provided by the application server, as described below in greater detail.

In the present exemplary embodiment, service pricing information database 114*m* is used to maintain information records with extensive medical cost data for an exhaustive set of healthcare services that can be offered by providers registered with server system 110 for purchase by customer users registered with the server system, and cost adjustment information database 114*n* is used to maintain a comprehensive set of data pertaining to location-based pricing adjustments that can be applied to the medical cost data maintained in service pricing information database 114*m* based on, for example, geographic zones or particular facilities within which healthcare services may be performed. In exemplary embodiments, the respective information records for healthcare services that are maintained in service pricing information database 114*m* and the information that populates the respective information record for each service can be created and maintained by a back-end administrator of server system 110.

The cost adjustment data can, for instance, be compiled from and/or determined based upon the Geographic Practice Cost Indices (GPC is), which is used along with RVUs in Medicare Physician Fee Schedule (PFS) provided by CMS to determine allowable payment amounts for medical procedures in a manner that reflects geographical variations in practice cost. In exemplary embodiments, a specific cost adjustment factor can be determined based on the GPCI information for each designated locality area and maintained within cost adjustment information database 114*n*. For example, a standard rate adjustment factor for each designated locality area can be determined by calculating an average (or any other suitable aggregate- or composite-based) factor by which the corresponding GPC is for the locality impact the standard national rate derived for each service. To account for geographic differences in input prices in determining allowable payment amounts for facility outpatient services, CMS further adjusts a labor portion of the national unadjusted payment rate (60 percent) by a facility wage index for the area where payment is being made (the remaining 40 percent non-labor portion is not adjusted).

In another example, for each service for which the information record within service pricing information database 114*m* includes an indication that the service is offered as a primary service of a bundled set of services along with an indication that a secondary service associated with the primary service is an anesthesia procedure, the respective pricing information that is included in the information record for the associated anesthesia procedure can be compiled from the anesthesia pricing information that is maintained by CMS. For this purpose, different types of services involving administration of anesthesia are assigned corresponding CPT codes, and each anesthesia code is assigned a base unit that reflects the difficulty of the procedure and inherent risks. For determining allowable payment amounts for anesthesia services, CMS utilizes the following formula:

(Time Units+Base Units)×Conversion Factor=Anesthesia Fee Amount.

As described above, healthcare marketplace system 100 is implemented as a client/server system that includes central server system 110, which is commonly accessed by each user of the system through operation of any of client systems 140 that are operatively coupled to the central server system via a communication network 150. Each client system 140 is a user terminal or other client device implementing software for and running a respective client application 142 for accessing services provided via a network-based application (also referred to herein as a network service) implemented by application server 116, and application server 116 can implement a user interface on the client application within which the client application renders the information served by the application server so that users of connected client systems 140 can access various services provided by the application server with relative ease by operating a corresponding client application 142. In exemplary embodiments, the user interface can be a web-based user interface, implemented as a web-based software application hosting a corresponding website that provides a number of web pages (that is, screens) to offer the services implemented by application server 116 to users. For example, a user can access the corresponding website and, thereby, the services provided by the application server using a web browser implemented within a client application 142 executing on a client system 142.

In particular, upon the provider user indicating an intention to utilize the pricing tool 137 in conjunction with offering healthcare services for purchase via server system 110 (for example, by selecting a "Service Pricing Tool" tab within the provider account page implemented by provider portal 130), the user will be directed to an interactive service pricing page with information that is generated based on the information maintained in the respective information record for the provider within the corresponding profile database maintained within data store 114 and the respective information records for healthcare services that are maintained in service pricing information database 114*m*. Pricing tool 137 may be configured, for example, to implement the interactive service pricing page to provide the provider user with detailed pricing information and recommended rates for services that may be offered by the provider for purchase via server system 110, as well as various user interface controls accessible by the user to perform adjustments to the recommended rates as desired.

FIG. 7A is a screen shot illustrating a first example of a graphical user interface provided by such a service pricing page 700 for a user accessing provider portal 130 in association with a registered hospital system account. In the example illustrated in FIG. 7A, the user interface provided at service pricing page 700 includes a medical specialty drop-down menu 702, a locality adjustment section 704, a recommended rate adjustment section 706, a detailed pricing information section 708, and a set of selectable buttons 710*a* ("Email Prices"), 710*b* ("Save Changes"), and 710*c* ("Take Live"), the use of which will be described in greater detail below. Drop-down menu 702 provides a list of selectable medical specialties (for example, orthopedics, general surgery, cardiac imaging, etc.), and pricing tool is implemented to, in response to the user selecting a particular medical specialty using drop-down menu 702, configure the user interface options and populate the information displayed within locality adjustment section 704, recommended rate adjustment section 706, and detailed pricing information section 708 in accordance with the selected medical specialty and further based on information maintained in the respective information record for the provider that is maintained within hospital system profile database 114*d*, information that is maintained in the respective information records for each service indicated as being commonly associated with the selected medical specialty within service pricing information database 114*m*, and information maintained within cost adjustment information database 114*n*, which, as discussed above, can be accessed by pricing tool 137 via database services provided at a front end by database server 112.

For instance, in the example screen shot illustrated in FIG. 7A, the user has selected "Radiology" from medical specialty drop-down menu 702, and pricing tool 137 has, in response to this selection, configured the user interface options and populated the information displayed within locality adjustment section 704, recommended rate adjustment section 706, and detailed pricing information section 708 in accordance with the selection of "Radiology" from drop-down menu 702. More specifically, as shown in FIG. 7A, locality adjustment section 704 has been configured to include a physician locality section and a facility section in response to the selection of "Radiology" from drop-down menu 702. The physician locality section is provided for making pricing adjustments based on the locality of a physician that is affiliated with the hospital system and would be performing the radiology services being priced. The facility section is included within locality adjustment section 704 in response to pricing tool 137 recognizing that the respective information records for services indicated as being commonly associated with the selected medical specialty of radiology within service pricing information database 114*m* include information records having an indication that the service is a primary service of a bundled set of services that is required to be performed at an outside facility and is provided for making pricing adjustments based on the facility that is affiliated with the hospital system at which the radiology services being priced would be performed.

In the present example, the physician locality section includes a physician location field 704*a* and a physician location rate field 704*b*, and the facility section includes a facility field 704*c* and a facility rate field 704*d*. The physician location field 704*a* is for receiving and displaying an entry specifying the location of a physician that would be performing the services indicated as being commonly associated with the selected medical specialty of radiology within service pricing information database 114*m*, and the physician location rate field 704*b* is configured to provide a rate adjustment factor for the pricing information included in detailed pricing information section 708 for the services indicated as being commonly associated with radiology. In exemplary embodiments, pricing tool 137 can be configured to derive an initial physician location entry based on the location associated with physician affiliation(s) included in hospital system profile database 114*d* and include this derived physician location entry as a default value within physician location field 704*a*. Physician location rate field 704*b* is provided for receiving and displaying a geographic adjustment rate for physician services that, by default, is derived based on information maintained in cost adjustment information database 114*n* and provided by pricing tool 137 in correspondence with the physician location entry that is currently specified within physician location field 704*a*. More particularly, in exemplary embodiments, pricing tool 137 can be configured to access the physician rate cost adjustment data in cost adjustment information database 114*n* that corresponds to the physician location entry that is currently specified within physician location field 704*a* (for example, a standard rate adjustment factor determined for a designated locality area that encompasses the specified physician location entry) and derive a corresponding geographic adjustment rate that is displayed as a default value within physician location rate field 704*b*.

In the present example, pricing tool 137 is further configured to allow the provider user accessing service pricing page 700 to proceed to enter text corresponding to a desired location of the physician that would perform the services associated with the selected medical specialty within physician location field 704*a*. In this regard, pricing tool 137 may be configured to require that the text entered by the user in physician location field 704*a* correspond to a particular locality area for which corresponding physician rate adjustments are maintained in cost adjustment information database 114*n*. In exemplary embodiments, the list of suggested physician locations provided by pricing tool 137 can further include an option for the user to select a standard, national physician rate rather than a particular geographic location. In response to a specification of a new physician location within physician location field 704*a*, pricing tool 137 can be configured to dynamically access the physician rate cost adjustment data in cost adjustment information database 114*n* that corresponds to the newly-specified physician location entry that is currently specified within physician location field 704*a* and derive a corresponding geographic adjustment rate that is displayed as the current value within physician location rate field 704*b*. In exemplary embodiments, pricing tool 137 can be configured to derive an initial outside facility entry based on the facility affiliation(s) included the respective information record for the hospital system account in hospital system profile database 114*d* being used to access the pricing tool 137 functionality via provider portal 130 and include this derived facility entry as a default value within facility field 704*c*. Facility rate field 704*d* is provided for receiving and displaying an adjustment rate for facility services that, by default, is derived and provided by pricing tool 137 in correspondence with the characteristics of the facility that is currently specified as the entry within facility field 704*c*.

In the present example, pricing tool 137 is further configured to allow the provider user accessing service pricing page 700 to proceed to enter text corresponding to a name of a desired outside facility at which the services associated with the selected medical specialty would be performed within facility field 704*c*. In this regard, pricing tool 137 may be configured to require that the text entered by the user in facility field 704*c* correspond to the name of a particular facility specified in the facility affiliations included the respective information record for the hospital system account in hospital system profile database 114*d* being used to access the pricing tool 137 functionality via provider portal 130.

With continued reference to the example screen shot illustrated in FIG. 7A, pricing tool 137 has, in response to the user selection "Radiology" from medical specialty drop-down menu 702, configured the user interface options and populated the information displayed within rate adjustment section 706. More specifically, as shown in FIG. 7A, rate adjustment section 706 has been configured to include a physician rate adjustment field 706*a* and a facility rate adjustment field 706*b* in response to the selection of "Radiology" from drop-down menu 702. Physician rate adjustment field 706*a* is provided for making a general pricing adjustment to the pricing information included in detailed pricing information section 708 for physician fees for the services indicated as being commonly associated with radiology as desired by the provider user that may be based on any budgetary considerations specific to the provider and/or physician.

With continued reference to the example screen shot illustrated in FIG. 7A, as noted above, pricing tool 137 has, in response to the user selection "Radiology" from medical specialty drop-down menu 702, configured the user interface options and populated the information displayed within detailed pricing information section 708. In general, as shown in FIG. 7A, detailed pricing information section 708 is generated by pricing tool 137 as a table with various interactive user interface controls that includes a procedure column 711, a facility price column 712, a physician price column 713, an additional fee column 714, and a total amount column 715.

The information in procedure column 711 is generated by pricing tool 137 to include a row entry for each procedure category listed in the respective information records for services that are maintained in service pricing information database 114m and include an indication that the service is commonly associated with the medical specialty selected via drop-down menu 702, which is "Radiology" for the example screen shot depicted in FIG. 7A For instance, the procedure categories listed in procedure column 711 in the present example include "Bone Density DXA Extremity" radiology procedures, "Bone Density DXA Scan" radiology procedures, and "Videofluoroscopic Swallowing Study" radiology procedures. As further illustrated in FIG. 7A for the example of the "Bone Density DXAExtremity" radiology procedures listing in in procedure column 711, detailed pricing information section 708 is implemented to include user interface elements that are accessible by the user.

In the present example, the expanded information for the "Bone Density DXAExtremity" radiology procedures listing includes row entries for a "Dxa bone density/peripheral" service and a "Fracture assessment via dxa" service. As further illustrated in FIG. 7A, the expanded information for a particular procedure category further includes, for each service categorized as a sub-procedure of the procedure category, a medical code number used to identify the service (for example, a CPT code), a base facility rate, a base physician rate, an adjusted facility rate, and an adjusted physician rate. The base physician rate for each service listed in the expanded display is obtained by pricing tool 137 from standard national physician rate derived for the service, and the adjusted physician rate for each service listed in the expanded display is calculated by pricing tool 137 for display within detailed pricing information section 708 by multiplying the corresponding base physician rate by both the current value that is specified in physician location rate field 704b of locality adjustment section 704 and the current percentage value that is specified in physician rate adjustment field 706a of recommended rate adjustment section 706. In the present example, as further illustrated in FIG. 7A, the expanded information for a particular procedure category further includes a physician price field 711a that specifies a price that will be set by the provider user for each of the services that have been categorized under the expanded procedure category and a facility price field 711b that specifies a price that will be applied by the provider user for the use of an outside facility for each of the services that have been categorized under the expanded procedure category.

In exemplary embodiments, pricing tool 137 can be configured to derive and include initial, default price values within physician price field 711a and physician price field 711a. As further indicated in the example screen shot illustrated in FIG. 7A, the row entry for a particular procedure category will include a pricing value under physician price column 713 that corresponds to the pricing value that is specified within physician price field 711a in the expanded display for the procedure category, and, likewise, the row entry for a particular procedure category will include a pricing value under facility price column 712 that corresponds to the pricing value that is specified within facility price field 711b in the expanded display for the procedure category. In this regard, pricing tool 137 can be configured to dynamically update the pricing values provided under physician price column 713 and facility price column 712 in response to changes to the price values within physician price field 711a and facility price field 711b respectively.

As further illustrated in FIG. 7A, the row entry for a particular procedure category can include a pricing value under total amount column 715 that is provided as a sum of the price values listed under facility price column 712, physician price column 713, and, if included, additional fee column 714 in the row entry for a particular procedure category. This represents the actual price at which each service listed in the expanded display for a procedure category would be offered for purchase via marketplace system 100 as a bundled set of services from the provider user accessing service pricing page 700 via provider portal 130.

As noted above and further illustrated in FIG. 7A, the user interface provided at service pricing page 700 in the present example also includes a set of accessible user interface controls 710a ("Email Prices"), 710b ("Save Changes"), and 710c ("Take Live"). For purposes of the present example, these user interface controls are provided within service pricing page 700 as selectable buttons. In the present exemplary embodiment, pricing tool 137 can be configured to, in response to a provider user selecting "Save Changes" button 710b, generate an information record that includes indications of all of the information. In the present exemplary embodiment, pricing tool 137 can be configured to, in response to a provider user selecting "Email Prices" button 710a, provide user interface controls for allowing the user to specify an email address and send an electronic document that includes indications of the pricing information.

Finally, with reference to the present example, pricing tool 137 can be configured to, in response to a provider user selecting "Take Live" button 710c, automatically initiate, on behalf of the provider user, a service offering with procedure management service 133 to offer each of the services currently included within detailed pricing information section 708 of service pricing page 700 for the particular medical specialty presented selected by the user from drop-down menu 702 for purchase via server system 110 In this manner, pricing tool 137 can provide a mechanism for a provider to offer a large number of services for purchase via marketplace system 100 by customer users registered with the system without having to perform full set of operations described above for accessing functionality provided by procedure management service 133 to offer each of the services individually.

FIG. 7B is a screen shot illustrating a second example of a graphical user interface provided by service pricing page 700 for a user accessing provider portal 130 in association with a registered hospital system account. In the example illustrated in FIG. 7B, the user has selected "General Surgery" from medical specialty drop-down menu 702, and pricing tool 137 has, in response to this selection, configured the user interface options and populated the information displayed within locality adjustment section 704, rate adjustment section 706, and detailed pricing information section 708 in accordance with the selection of "General Surgery" from drop-down menu 702. More specifically, as shown in FIG. 7B, locality adjustment section 704 has been configured to include, in addition to the physician locality section and the facility section described above with reference to the example illustrated in FIG. 7C, an anesthesia locality section in response to the selection of "General Surgery" from drop-down menu 702. The anesthesia locality section is included within locality adjustment section 704 in response to pricing tool 137 recognizing the respective information records for services.

In the present example, the anesthesia locality section includes an anesthesia location field 704e and an anesthesia location rate field 704f. The anesthesia location field 704e is for receiving and displaying an entry specifying the location at which the services indicated as being commonly associated with the selected medical specialty of general surgery within service pricing information database 114m would be performed, and the anesthesia location rate field 704f is configured to provide a rate adjustment factor for the pricing information included in detailed pricing information section 708 for the services indicated as being commonly associated with radiology. Anesthesia location rate field 704f is provided for receiving and displaying a geographic adjustment rate for physician services that, by default, is derived and provided by pricing tool 137 in correspondence with the anesthesia location entry that is currently specified within anesthesia location field 704e. More particularly, in exemplary embodiments, pricing tool 137 can be configured to access the information pertaining to anesthesia rate adjustments in service pricing information database 114n corresponding to the anesthesia location entry that is currently specified within anesthesia location field 704e and derive a corresponding geographic adjustment rate that is displayed as a default value within anesthesia location rate field 704e. The corresponding geographic adjustment rate can be derived, for example, based on a ratio of the CMS anesthesia conversion factor to a standard, national anesthesia conversion factor.

In response to a specification of a new location within anesthesia location field 704e, pricing tool 137 can be configured to dynamically access the information pertaining to physician rate adjustments in geographic factors database 114n corresponding to the newly-specified physician location entry within anesthesia location field 704e and derive a corresponding geographic adjustment rate that is displayed as the current value within anesthesia location rate field 704f. With continued reference to the example screen shot illustrated in FIG. 7B, as noted above, pricing tool 137 has, in response to the user selection "General Surgery" from medical specialty drop-down menu 702, configured the user interface options and populated the information displayed within rate adjustment section 706. More specifically, as shown in FIG. 7B, rate adjustment section 706 has been configured to include, in addition to a physician rate adjustment field 706a and a facility rate adjustment field 706b as described above with reference to the example screen shot shown in FIG. 7A, an anesthesia rate adjustment field 706c in response to the selection of "Radiology" from drop-down menu 702. Anesthesia rate adjustment field 706c is included within rate adjustment section 706 in response to pricing tool 137 recognizing that the respective information records for services indicated as being commonly associated with the selected medical specialty of general surgery within service pricing information database 114m include information records having an indication that the service is a primary service of a bundled set of services for which a secondary service associated with the primary service in the bundled set is an anesthesia procedure and is provided for making a general pricing adjustment to the pricing information included in detailed pricing information section 708 for anesthesia fees for the services indicated as being commonly associated with general surgery as desired by the provider user that may be based on any budgetary considerations specific to the provider or physician.

With continued reference to the example screen shot illustrated in FIG. 7B, as noted above, pricing tool 137 has, in response to the user selection "General Surgery" from medical specialty drop-down menu 702, configured the user interface options and populated the information displayed within detailed pricing information section 708. In general, as shown in FIG. 7B, detailed pricing information section 708 is generated by pricing tool 137 as a table with various interactive user interface controls that includes, in addition to procedure column 711, facility price column 712, physician price column 713, additional fee column 714, and total amount column 715, an anesthesia price column 716. As illustrated in FIG. 7B, the expanded information for a particular procedure category further includes, for each service categorized as a sub-procedure of the procedure category, in addition to a medical code number used to identify the service, a base facility rate, a base physician rate, an adjusted facility rate, and an adjusted physician rate as described above with reference to FIG. 7A, a base anesthesia rate and an adjusted anesthesia rate. In the present example, as further illustrated in FIG. 7B, the expanded information for a particular procedure category further includes, in addition to physician price field 711a and facility price field 711b, an anesthesia price field 711c that specifies a price that will be applied by the provider user for each anesthesia service performed in association with the services that have been categorized under the expanded procedure category. For example, pricing tool 137 can be configured to enable the user select between using the average of the corresponding adjusted anesthesia rates for all services listed in the expanded display for a procedure category for the price values within anesthesia price field 711c or the highest of the corresponding adjusted anesthesia rates for all services listed in the expanded display for a procedure category for the price values within anesthesia price field 711c. In exemplary embodiments, pricing tool 137 can be further configured to allow the provider user accessing service pricing page 700 to access anesthesia price field 711c to input a particular price value within this field.

As further indicated in the example screen shot illustrated in FIG. 7B, the row entry for a particular procedure category will include a pricing value under anesthesia price column 716 that corresponds to the pricing value that is specified within anesthesia price field 711c in the expanded display for the procedure category. As further illustrated in FIG. 7B, the row entry for a particular procedure category can include a pricing value under total amount column 715 that is provided as a sum of the price values listed under facility price column 712, physician price column 713, anesthesia price column 716, and, if included, additional fee column 714 in the row entry for a particular procedure category. FIG. 7C is a screen shot illustrating a third example of a graphical user interface provided by service pricing page 700 for a user accessing provider portal 130 in association with a registered hospital system account. In the example illustrated in FIG. 7C, the user has selected "GI" (gastroenterology) from medical specialty drop-down menu 702, and pricing tool 137 has, in response to this selection, configured the user interface options and populated the information displayed within locality adjustment section 704, rate adjustment section 706, and detailed pricing information section 708 in accordance with the selection of "GI" from drop-down menu 702. In general, as shown in FIG. 7C, detailed pricing information section 708 is generated by pricing tool 137 as a table with various interactive user interface controls that includes, in addition to procedure column 711, facility price column 712, physician price column 713, additional fee column 714, and total amount column 715, a pathology price column 717.

As illustrated in FIG. 7C, the expanded information for a particular procedure category further includes, for each service categorized as a sub-procedure of the procedure category, in addition to a medical code number used to identify the service, a base facility rate, a base physician rate, an adjusted facility rate, and an adjusted physician rate as described above with reference to FIG. 7A, a base pathology rate. The base pathology rate for each service listed in the expanded display is obtained by pricing tool 137 from the pathology rate for the service that is stored within the respective information record maintained for the service within service pricing information database 114*m* for display within detailed pricing information section 708.

In the present example, as further illustrated in FIG. 7C, the expanded information for a particular procedure category further includes, in addition to physician price field 711*a* and facility price field 711*b*, a pathology price field 711*d* that specifies a price that will be applied by the provider user for each pathology service performed in association with the services that have been categorized under the expanded procedure category. For example, pricing tool 137 can derive and set the default price value within pathology price field 711*d* as the average of the base pathology rates for all services listed in the expanded display for a procedure category. In exemplary embodiments, pricing tool 137 can be further configured to allow the provider user accessing service pricing page 700 to access pathology price field 711*d* to input a particular price value within this field.

As further indicated in the example screen shot illustrated in FIG. 7C, the row entry for a particular procedure category will include a pricing value under pathology price column 717 that corresponds to the pricing value that is specified within pathology price field 711*d* in the expanded display for the procedure category. In this regard, pricing tool 137 can be configured to dynamically update the pricing value provided under pathology price column 717 in response to changes to the price value within pathology price field 711*d*. As further illustrated in FIG. 7B, the row entry for a particular procedure category can include a pricing value under total amount column 715 that is provided as a sum of the price values listed under facility price column 712, physician price column 713, pathology price column 717, and, if included, additional fee column 714 and anesthesia price column 716 in the row entry for a particular procedure category. This represents the actual price at which each service listed in the expanded display for a procedure category would be offered for purchase as a bundled set of services via marketplace system 100 from the provider user accessing service pricing page 700 via provider portal 130. In this regard, service selling service 135 may provide functionality allowing a user of a hospital system account to sell, in addition to services that are offered for purchase by the hospital within server system 100, services that are constructed by a user of a hospital system account, including bundled sets of services.

In exemplary embodiments, the user interface implemented by account management service 131 may be further configured to provide user interface controls for requesting authorization for payment of a predetermined fee to gain access to the ability to offer healthcare products for purchase within marketplace system 100. Such a fee may be, for example, a one-time charge or a periodic charge (such as a monthly, biannual, or annual fee). Upon the user indicating an intention to offer a healthcare product for purchase (for example, by selecting a "Offer Service" tab within the pharmacy account page implemented by provider portal 130), the user will be able to initiate a product offering with product management service 134 to offer a healthcare product for purchase via server system 110.

Purchasing service 126 can be also be configured to generate a respective information record for the completed purchase with corresponding information within transaction information database 114*k*, which may, in some exemplary embodiments, initially indicate that the purchase has not yet been redeemed with respect to a purchase of an individual product or with respect to each product that is included in a purchase of a bundled set, and generate a voucher for the customer user to use with respect to the purchased product to redeem the purchase by receiving the product from the pharmacy. Such a voucher can include a confirmation number or other redemption code for the purchase.

Upon the user indicating an intention to request processing of payment for a purchased product that has been provided (for example, by selecting a "Voucher Processing" tab within the pharmacy account page implemented by provider portal 130), the user will be able to initiate a voucher processing session with transaction processing service 136.

FIG. 8 illustrates a flow chart of insurance policy stored in the insurance database (114*o*, shown in FIG. 2) executed by the application server (116, shown in FIG. 2). The insurance database is programmed to provide optimized bundled price 802. For exemplary purposes, the system maximizes collections at each phase in the care cycle.

For various phases there is an option for paying the payment 804. The patient is referred or scheduled for a procedure, where the patient may receive a push notification to pay prospectively. Alternatively, the patient checks-in at provider and the patient pays at the point of service either via cash, card, digital wallet etc. Alternatively, the patient is made to pay at discharge wherein, the patient receives a push notification to pay retrospectively.

Further, each of the patient information is monitored such as doctor's order/schedule (for example, CHC Redox), propensity to pay data (CHC-Vendor), benefit status (CHC-ribbon health) and care credit pre-approval. Based on the patient information, doctor's order is matched. Further, the price is set based on the patient's capacity/willingness to pay for the service/product. Further, each payment is monitored to check if patient is paying out-of-pocket. The system compares the bundle price to the remaining patient deductible to determine the patient's capacity to pay for the services/product. Furthermore, the patients are allowed to pay either in full or through CareCredit.

The system makes sure to pay the optimal price in full every time to the hospital/physician/pharmacy and any associated service provider. The procedure is transparent and acceptable to both patients and the hospital. The service providers collect the maximum data of patients who are willing to pay. Further, the hospital leaves revenue on the table by charging less than what patients are willing to pay.

The application server (116, shown in FIG. 2) processes the data stored in the insurance database 114o and allow the user to excess the insurance information via an insurance management (14, shown in FIG. 2). The hospital sends an electronic claim to the system after care is delivered to the patient. The system then distributes payment and sends electronic remittance file based on the information stored in the insurance database 114o. The system passes the electronic claim to the insurance company 806 to update patient's accumulator (not for reimbursement). The insurance 806 then notifies the system of accumulator status. The system then sends update to the patients.

Figure 9:
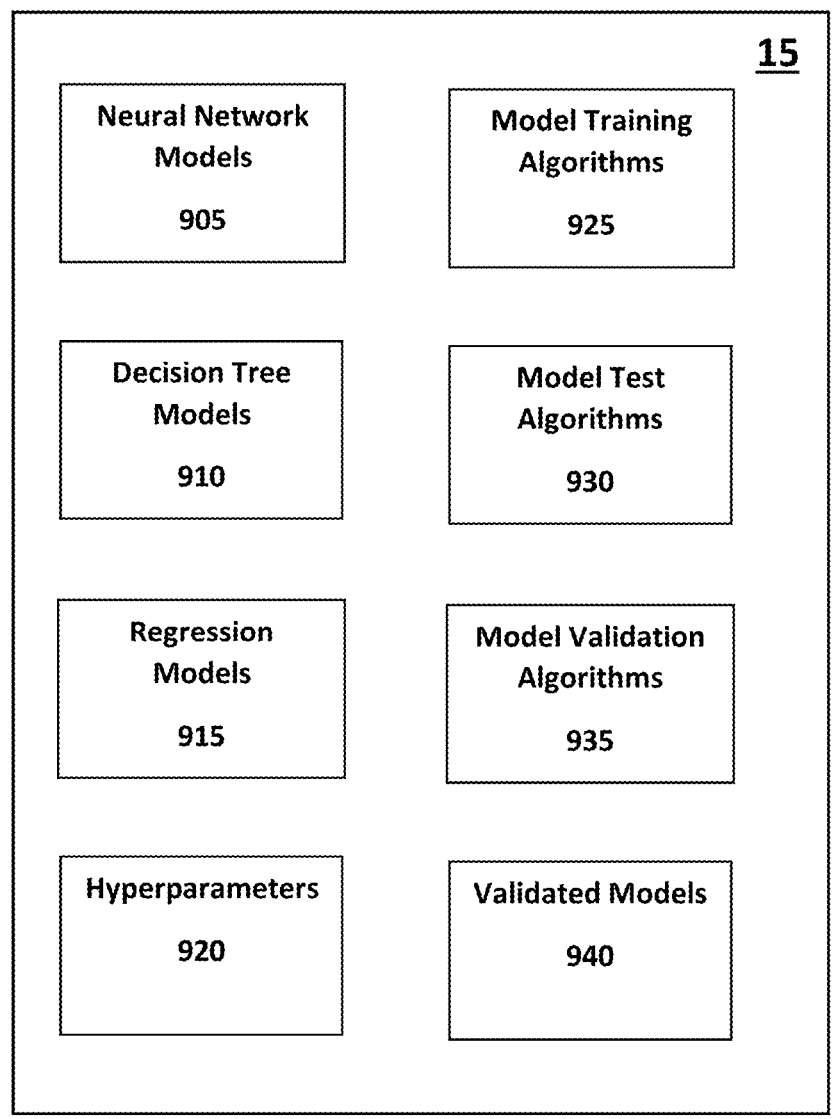
FIG. 9 depicts a block diagram detail view of an exemplary machine learning module.

FIG. 9 depicts a block diagram detail view of an exemplary machine learning module. In FIG. 9, the exemplary machine learning module 15 comprises processor executable program instructions and data configured to implement various types of machine learning models including but not limited to neural network models 905, decision tree models 910, and regression models 915. In the depicted implementation the neural network models 905 may comprise convolutional neural network (CNN) models, recurrent neural network (RNN) models, and long short-term memory (LSTM) models. In the depicted implementation the machine learning module 15 comprises decision tree models 910. The decision tree models 910 may include individual classification and regression tree (CART) models trained for regression or classification as individual decision models. The decision tree models 910 may include a random forest of CART models trained for classification or regression as a set of decision models. An exemplary implementation may configure a random forest for a predetermined population of patients wherein each decision tree of the plurality of decision trees may determine a prediction concerning a particular patient of the patient population. In an implementation the plurality of predictions by the random forest may be used to determine a condition trend for the population and the condition trend for the population may be used to optimize cost or outcome for the population modeled using the random forest. The regression models 915 may include linear, polynomial, logistic, and multinomial regression models. The regression models may be configured for and used for predicting whether a patient's condition is likely to improve based on predicting a condition trend for the patient using healthcare outcome and patient condition data as described herein. In the depicted implementation the machine learning module 15 further comprises hyperparameters 920 governing the structure, training, and function of the machine learning models. For example the hyperparameters 920 may comprise one or more loss functions, learning rates, topologies, number of training passes (epochs), stopping criteria, activation functions and initial weights and/or biases.

In the depicted implementation the machine learning model 15 comprises processor executable program instructions and data configured to implement model training algorithms 925 comprising at least gradient descent, backward propagation and forward propagation. In the depicted implementation the machine learning model 15 comprises processor executable program instructions and data configured to implement the model test algorithms 930 and model validation algorithms 935. In an illustrative example the model test algorithms 930 may include comparing model output determined as a function of labeled test data input (for example test data points labeled with known correct output) with the respective known correct output based on the label. The model validation algorithms 935 may include cross-validation. The model validation algorithms 935 may include comparing model output determined as a function of hold-out or out of bag data with output determined from another validated model. For example a decision tree trained to model a human physician's diagnosis decisions for a plurality of conditions may be used to validate as medically necessary or not contraindicated care or tests recommended by an exemplary recommender engine implementation. The machine learning module 15 may provide access to validated models 940 for use by an exemplary recommender engine implementation to predict likely conditions determined as a function of patient data input.

An exemplary machine learning module 15 implementation may comprise one or more machine learning model. The one or more machine learning model may comprise a neural network. The neural network may comprise a deep-leaning neural network. The neural network may comprise a plurality of neural network layers. The plurality of neural network layers may comprise an input layer. The plurality of neural network layers may comprise one or more hidden layer. The plurality of neural network layers may comprise one or more convolutional layer. The one or more convolutional layer may be configured with a plurality of inputs coupled with a respective plurality of data elements. The plurality of neural network layers may comprise one or more recurrent layer. The one or more recurrent layer may be configured with a plurality of inputs coupled with a respective plurality of time-series data sources. The plurality of neural network layers may comprise a fully connected layer. The plurality of neural network layers may comprise an output layer. The neural network may comprise an LSTM. The LSTM may be configured with a plurality of inputs configured in communication with a respective plurality of time-series data sources.

The plurality of inputs to the neural network may comprise healthcare outcomes and patient condition from individual care episodes. Each care episode may be related to care for a particular condition. For example, an individual care episode may comprise a plurality of encounter data points disposed in a time series format. The plurality of encounter data points related to care for the particular condition may begin with an encounter data point captured when the condition was diagnosed, continue through a series of encounter data points capturing data from events comprising treatment such as surgery and recovery, and may end with a final encounter data point when care for the condition ends. The healthcare outcomes and patient condition data from each encounter of each care episode may be provided to the neural network in a time-series of data points. Healthcare outcome and condition data points from each care episode of a plurality of care episodes may be applied to a respective plurality of neural network inputs, wherein each time-series data point represents a single patient care encounter and each input receives time-series data points from one episode. In an illustrative example a care episode may comprise care for a condition distributed over a plurality of encounters during a period of time.

The plurality of inputs to the neural network may comprise healthcare outcomes from a respective plurality of care episodes wherein each care episode comprises a plurality of healthcare services from a selectively redeemable bunded set of services. Each encounter data point may comprise patient condition data prior to and current with the encounter, in-line with what has been disclosed herein. An exemplary implementation may be configured to compare patient condition data prior to and current with the encounter to determine if the patient condition trend is stable, deteriorating, improving, or reached goal. In an illustrative example, an implementation may be configured to determine a patient condition trend is stable if current patient data such as but not limited to blood pressure, blood test results, weight, or patient-reported conditions such as pain or range of movement, have not changed substantially from the prior patient data. An implementation may be configured to determine a patient condition trend is deteriorating if current patient data is further from a goal patient data value than the prior patient data. An implementation may be configured to determine a patient condition trend is improving if current patient data is closer to a goal patient data value than the prior patient data. An implementation may be configured to determine a patient condition trend has reached goal if current patient data is substantially the same as a goal patient data value. An implementation may be configured to recommend care corresponding to a condition determined by the system to be deteriorating. In some implementations a predetermined threshold probability may be used to determine if the patient condition trend has reached a level at which care should be recommended. In an illustrative example the distribution of patient condition trends represents the probability a patient would have a condition at a given point in time.

An implementation may be configured to label patient condition changes determined for each encounter in a time-series of encounters as stable, deteriorating, improving, or reached goal. An exemplary implementation may label patient condition data using any useful labels. The historical patient condition data may be used as training data for one or more machine learning model. For example, an implementation may be configured to create a training data set comprising healthcare outcomes from a plurality of patient healthcare episodes each comprising a plurality of procedures over a past time period and a plurality of patient condition data records sampled from the past time period, wherein the patient condition records for each encounter comprise patient condition data prior to and current with the encounter. An exemplary implementation may comprise using the labeled time-series patient condition data for the past time period in a supervised training mode to train one or more machine learning model to determine a probability distribution of patient condition trends for a future time period.

An exemplary implementation may comprise creating training data including at least healthcare outcome data and patient condition data. In an illustrative example healthcare outcome data may be time series data comprising a plurality of data points located on a timeline. In this example each healthcare outcome data point may comprise information identifying services performed, service date, current patient condition before the bundled services were performed and patient condition after the bundled services were performed. The patient condition after the bundled services were performed may be determined by medical tests or evaluation during the patient's next encounter, or the patient may self-report using a questionnaire, patient portal, or other digital communication with a caregiver. The healthcare outcome data may further comprise patient condition data related to the outcome data for a period of time. For example healthcare outcome data may comprise medical test result data for a six month period of time to support a determination the healthcare outcome was successful or reached goal. The patient condition data may be time-series data comprising a plurality of data points located on a timeline. The patient condition data may comprise patient-provided information including but not limited to patient reports to physicians/care coordinators, lab test data, and/or wearable device data. In an illustrative example one or more patient condition data point may be labeled to indicate a category of a patient's condition, such as well, minor condition, chronic condition, or severe condition. An exemplary implementation may be configured to contemplate any useful number or combination of condition categories. In this example the healthcare outcome data and patient condition data comprise healthcare outcome and related patient condition data collected in combination with proprietary selectively redeemable bundled services. That is, at least one healthcare outcome data point may comprise a healthcare outcome resulting from a service performed as a set of selectively redeemable bundled services.

Figure 10:
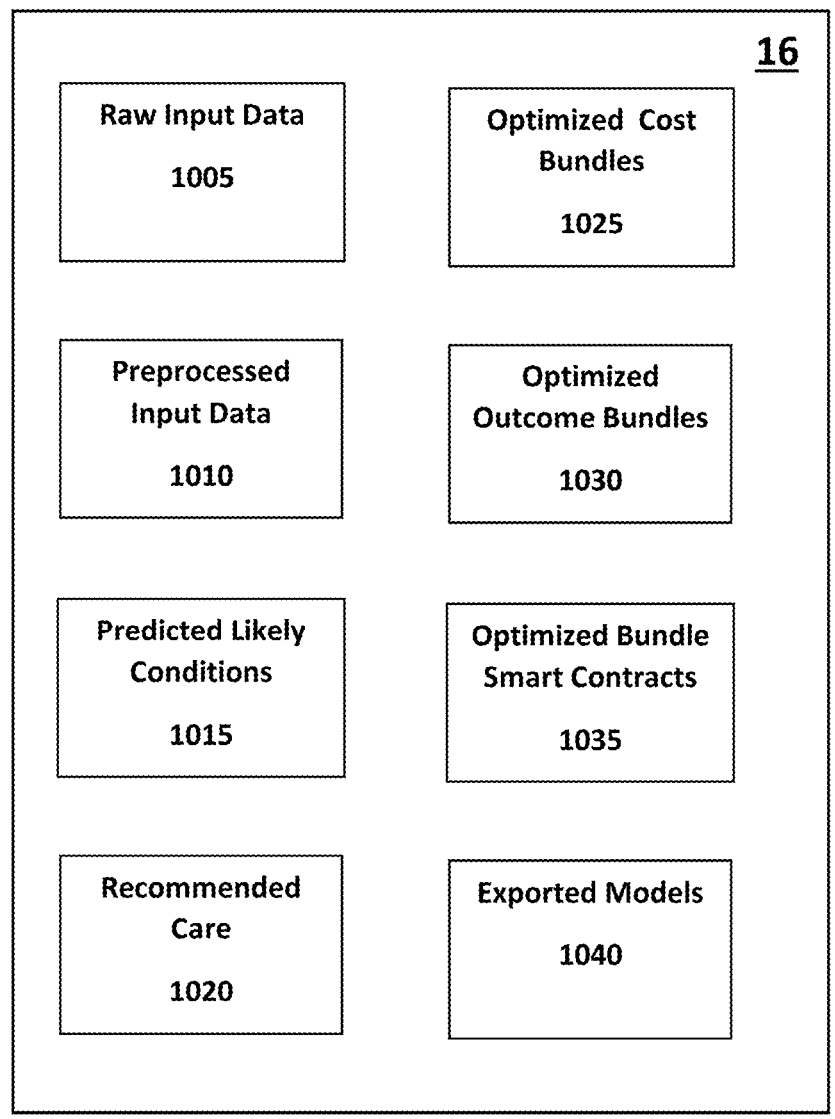
FIG. 10 depicts a block diagram detail view of an exemplary recommendation engine.

FIG. 10 depicts a block diagram detail view of an exemplary recommendation engine. In FIG. 10, the exemplary recommendation engine 16 comprises raw input data 1005. The raw input data may be medical data from an EMR or EHR, diagnosis data, blood pressure, heart rate, or other sensor-related data, wearable device data, lab test result data, or the like. An exemplary implementation may preprocess the raw input data 1005 to obtain the preprocessed input data 1010. An exemplary implementation may fill in missing values or replace anomalous (for example a reading that is far too high or low) data points with a local average to facilitate stable algorithmic processing. In some cases the data may be low-pass filtered to smooth peaks from the data to permit a machine learning model processing time-series data to converge or stabilize more quicky. In some cases an exemplary implementation may use techniques known in the art of sensor data fusion to merge data from multiple sensors or tests that have different ranges and meanings into a single value useful to the implementation for training, prediction, or recommendation. For example, some blood tests may be performed using different lab protocols with different numeric result ranges. An implementation may be configured to assign a score from a single merged range to test results from multiple different ranges and use the score from the single merged range as a qualitative categorical value such as severe, bad, mild, or good. In the depicted implementation the exemplary recommendation engine 16 also includes predicted likely conditions 1015 determined by one or more machine learning model in-line with what has been disclosed herein. In the depicted implementation the exemplary recommendation engine 16 also includes recommended care 1020 selected by the recommendation engine 16 to optimize a healthcare result parameter. For example, the recommendation engine 16 may be configured to select optimized cost bundles 1025 to optimize total healthcare cost for an individual or a population based on condition trends and data input. The recommendation engine 16 may be configured to select optimized outcome bundles 1305 to optimize healthcare outcomes independent of cost for an individual or a population based on the condition trends and data input. In the illustrated implementation the exemplary recommendation engine 16 may acquire and/or offer optimized bundle smart contracts 1035 determined to optimize a healthcare result parameter such as outcome or cost. The recommendation engine 16 may provide a third-party access to exported models 1040 for predicting condition trends and recommending care based on patient data input.

Figure 11:
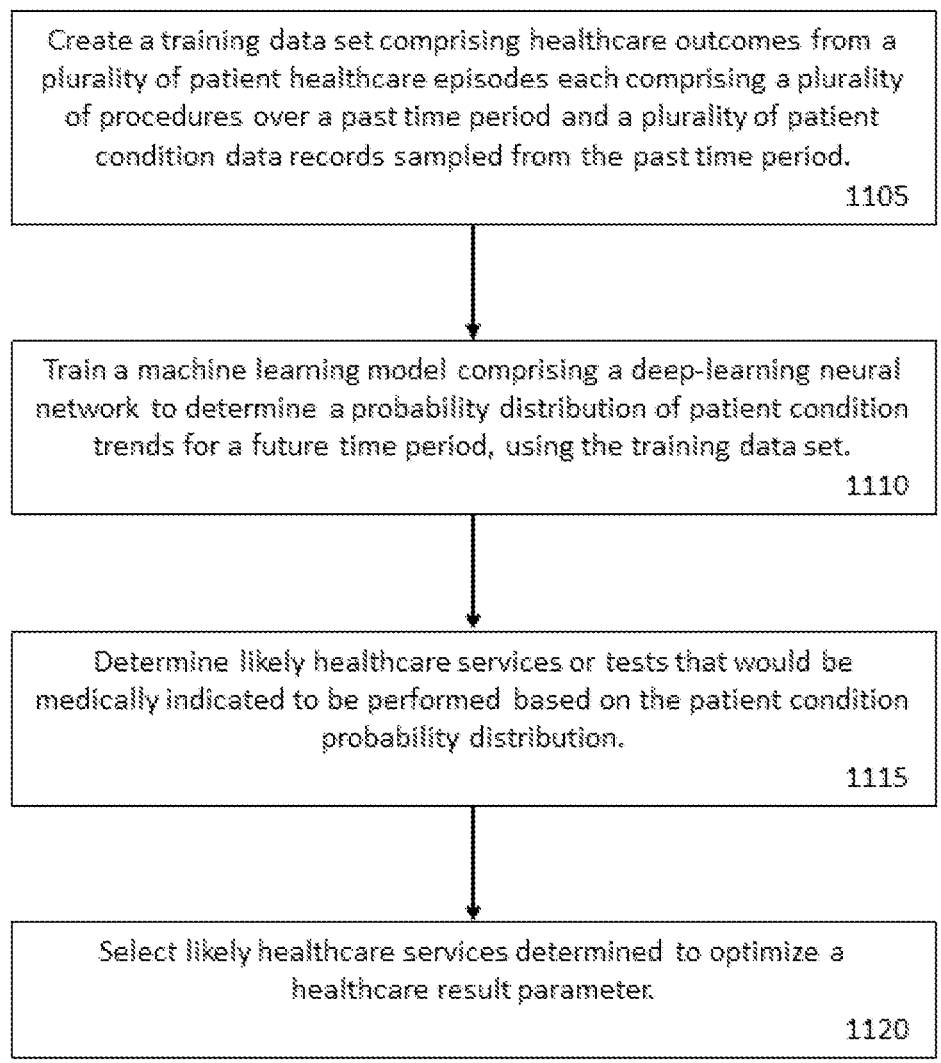
FIG. 11 depicts a process flow of an exemplary recommender system configured to recommend care for likely conditions predicted by a neural network trained using healthcare episode outcome data and patient condition data.

FIG. 11 depicts a process flow of an exemplary recommender system configured to recommend care for likely conditions predicted by a neural network trained using healthcare episode outcome data and patient condition data. In FIG. 11, the depicted method 1100 is illustrative of an example aspect of machine learning-based selectively redeemable healthcare service recommendation engine design. The method depicted in FIG. 11 is given from the perspective of an exemplary selectively redeemable bundled services recommendation engine (SRBSRE) implemented via processor-executable program instructions executing on the SRBSRE processor 604, depicted in FIG. 5. In various embodiments, the processor 604 implementing the process 1100 may be configured in an exemplary system 100 as described herein with reference to any of FIGS. 1, and 6. For example, the depicted process may execute as processor executable program instructions on processor 604 configured in the application server 116, depicted in FIGS. 1 and 6. In various implementations, the method depicted in FIG. 11 may also be understood as from the perspective of processor-executable program instructions executing on a mobile device operably coupled with the network 150, depicted at least in FIGS. 1 and 6. In the illustrated implementation, the SRBSRE executes as program instructions on the processor 604, depicted in FIG. 5. In some embodiments, the SRBSRE may execute as a cloud service communicatively and operatively coupled with system services, hardware resources, or software elements local to and/or external to the SRBSRE processor 604.

The depicted method begins at step 1105 with the processor 604 creating a training data set comprising healthcare outcomes from a plurality of patient healthcare episodes wherein each episode comprises a plurality of procedures over a past time period and a plurality of patient condition data records sampled from the past time period.

The method continues at step 1110 with the processor 604 training a machine learning model comprising a deep-learning neural network to determine a probability distribution of patient condition trends for a future time period, using the training data set.

The method continues at step 1115 with the processor 604 determining likely healthcare services or tests that would be medically indicated to be performed in the future time period, based on the probability distribution of patient condition trends.

The method continues at step 1120 with the processor 604 selecting likely healthcare services determined to optimize a healthcare result parameter over a predetermined time period for an individual patient or a patient population comprising a plurality of patients. The optimized healthcare result parameter may be healthcare outcome comprising optimizing medical condition. The optimized healthcare result parameter may be healthcare cost comprising optimizing total cost of healthcare.

In some implementations the method may repeat. In some cases the method may end.

In an aspect an exemplary method may comprise: generating, by at least one processor, a healthcare service recommendation comprising at least one recommended healthcare service determined as a function of patient information input to a recommendation engine comprising a machine learning model; generating, by the at least one processor, a purchase information record comprising an individual redemption status of each individual service of a bundled plurality of individual services, wherein the bundled plurality of individual services comprises at least the at least one recommended healthcare service; and generating, by the at least one processor, a machine-readable identifier uniquely associated with the purchase information record.

The method may further comprise providing, by the at least one processor, marketplace access to the machine-readable identifier.

Providing, by the at least one processor, marketplace access to the machine-readable identifier may further comprise providing access to receive each healthcare service of the bundled plurality of individual services individually.

The method may further comprise generating, by the at least one processor, machine-readable information useful for redemption of the purchase information record based on associating the machine-readable information with the machine-readable identifier.

The method may further comprise transmitting, by the at least one processor, machine-readable information useful for redemption of the purchase information record to at least one provider.

The machine-readable identifier may further comprise a confirmation number.

The machine-readable information useful for redemption of the purchase information record may further comprise an email, text message, or QR code.

The method may further comprise presetting, by the at least one processor, an initial individual redemption status of each individual service of the bundled plurality of individual services in the purchase information record to indicate each individual service has not been redeemed.

The purchase information record may persist in a data store operably coupled with the at least one processor and wherein the purchase information record may be redeemable at least until each of the healthcare services in the bundled plurality of individual services is redeemed.

The method may further comprise receiving, by the at least one processor, a request comprising machine readable information uniquely associated with the machine-readable identifier.

The request may further comprise a request to redeem the purchase information record with respect to at least one individual service of the bundled plurality of individual services.

The request may further comprise a request to determine the individual redemption status of at least one individual service of the bundled plurality of individual services.

The method may further comprise updating, by the at least one processor, the individual redemption status of at least one individual service of the bundled plurality of individual services in the purchase information record to indicate the at least one individual service has been redeemed.

The machine learning model may further comprise at least one neural network.

The at least one neural network may further comprise a deep-learning neural network.

The at least one neural network may be a trained neural network that was trained based on supervised training to predict likely patient conditions based on the patient information input.

The method may further comprise recommending, by the at least one processor, services or tests medically indicated for predicted likely conditions.

The supervised training may have further comprised using a training data set comprising a plurality of time-series healthcare outcome data points sampled during a past time period from a plurality of patient healthcare episodes.

The supervised training may have further comprised training the at least one neural network to determine a probability distribution of patient condition trends for a future time period using the training data set and labeled test data.

Each healthcare outcome data point of the plurality of time-series healthcare outcome data points may further comprise information identifying services performed, service date, and a patient condition data point comprising current patient condition before the bundled services were performed and patient condition after the bundled plurality of individual services were performed.

Each patient healthcare episode of the plurality of patient healthcare episodes may further comprise care for a condition distributed over a plurality of patient encounters during a period of time.

The at least one neural network may further comprise a plurality of neural network inputs.

The healthcare outcome data points and patient condition data points from each patient healthcare episode of the plurality of patient healthcare episodes may be applied respectively to the plurality of neural network inputs.

Each time-series patient condition data point may represent a single patient care encounter and each neural network input of the plurality of neural network inputs receives time-series data points from one episode.

Each patient condition data point may further comprise patient condition data prior to and current with the patient care encounter.

The supervised training may have further comprised creating the training data set.

Creating the training data set may have further comprised labeling patient condition changes with a label determined for each patient care encounter in a time-series of encounters as stable, deteriorating, improving, or reached goal.

The label may have been determined based on comparing patient condition data prior to and current with the patient care encounter to determine a patient condition trend.

The supervised training may have further comprised using the labeled time-series patient condition data for the past time period to train the at least one neural network to determine the probability distribution of patient condition trends for the future time period.

The method may further comprise offering or acquiring one or more smart contract for the at least one recommended healthcare service.

Aspects of exemplary embodiments of the present invention described herein can be implemented using one or more program modules and data storage units. As used herein, the term "modules", "program modules", "components", "systems", "tools", "utilities", and the like include routines, programs, objects, components, data structures, and instructions, or instructions sets, and so forth that perform particular tasks or implement particular abstract data types. As can be appreciated, the modules refer to computer-related entities that can be implemented as software, hardware, firmware and/or other suitable components that provide the described functionality, and which may be loaded into memory of a machine embodying an exemplary embodiment of the present invention. Aspects of the modules may be written in a variety of programming languages, such as C, C++, Java, etc. The functionality provided by modules used for aspects of exemplary embodiments described herein can be combined and/or further partitioned.

As used herein, the terms "data storage unit," "data store", "storage unit", and the like can refer to any suitable memory device that may be used for storing data, including manual files, machine readable files, and databases. The modules and/or storage units can all be implemented and run on the same computing system (for example, the exemplary computer system illustrated in FIG. 5 and described below) or they can be implemented and run-on different computing systems. For example, one or modules can be implemented on a personal computer operated by a user while other modules can be implemented on a remote server and accessed via a network.

Exemplary embodiments of the present invention can be realized in hardware, software, or a combination of hardware and software. Exemplary embodiments can be realized in a centralized fashion in one computer system or in a distributed fashion where different elements are spread across several interconnected computer systems. Any kind of computer system—or other apparatus adapted for carrying out the methods described herein—is suited. A typical combination of hardware and software could be a general-purpose computer system with a computer program that, when being loaded and executed, controls the computer system such that it carries out the methods described herein.

A computer system in which exemplary embodiments can be implemented may include, inter alia, one or more computers and at least a computer program product on a computer readable medium, allowing a computer system, to read data, instructions, messages or message packets, and other computer readable information from the computer readable medium. The computer readable medium may include non-volatile memory, such as ROM, Flash memory, Disk drive memory, CD-ROM, and other permanent storage. Additionally, a computer readable medium may include, for example, volatile storage such as RAM, buffers, cache memory, and network circuits. Furthermore, the computer readable medium may comprise computer readable information in a transitory state medium such as a network link and/or a network interface, including a wired network or a wireless network, that allow a computer system to read such computer readable information. While the invention has been described in detail with reference to exemplary embodiments, it will be understood by those skilled in the art that various changes and alternations may be made and equivalents may be substituted for elements thereof without departing from the scope of the invention as defined by the appended claims. In addition, many modifications may be made to adapt a particular application or material to the teachings of the invention without departing from the essential scope thereof.

Variations described for exemplary embodiments of the present invention can be realized in any combination desirable for each particular application. Thus particular limitations, and/or embodiment enhancements described herein, which may have particular limitations, need be implemented in methods, systems, and/or apparatuses including one or more concepts describe with relation to exemplary embodiments of the present invention.

Therefore, it is intended that the invention not be limited to the particular embodiments disclosed as the best mode contemplated for carrying out this invention, but that the invention will include all embodiments falling within the scope of the present application as set forth in the following claims, wherein reference to an element in the singular, such as by use of the article "a" or "an" is not intended to mean "one and only one" unless specifically so stated, but rather "one or more." Moreover, no claim element is to be construed under the provisions of 35 U.S.C. § 112, sixth paragraph, unless the element is expressly recited using the phrase "means for" or "step for." These following claims should be construed to maintain the proper protection for the present invention.

What is claimed is:

1. A method comprising:
 generating, by at least one processor, a healthcare service recommendation comprising at least one recommended healthcare service determined as a function of patient information input to a recommendation engine comprising a machine learning model;

generating, by the at least one processor, a purchase information record comprising an individual redemption status of each individual service of a bundled plurality of individual services, wherein the bundled plurality of individual services comprises at least the at least one recommended healthcare service; and generating, by the at least one processor, a machine-readable identifier uniquely associated with the purchase information record.

2. The method of claim 1, wherein the method further comprises providing, by the at least one processor, marketplace access to the machine-readable identifier.

3. The method of claim 2, wherein providing, by the at least one processor, marketplace access to the machine-readable identifier further comprises providing access to receive each healthcare service of the bundled plurality of individual services individually.

4. The method of claim 2, wherein the method further comprises generating, by the at least one processor, machine-readable information useful for redemption of the purchase information record based on associating the machine-readable information with the machine-readable identifier.

5. The method of claim 4, wherein the machine-readable information useful for redemption of the purchase information record further comprises an email, text message, or QR code.

6. The method of claim 2, wherein the method further comprises transmitting, by the at least one processor, machine-readable information useful for redemption of the purchase information record to at least one provider.

7. The method of claim 2, wherein the machine-readable identifier further comprises a confirmation number.

8. The method of claim 1, wherein the method further comprises presetting, by the at least one processor, an initial individual redemption status of each individual service of the bundled plurality of individual services in the purchase information record to indicate each individual service has not been redeemed.

9. The method of claim 1, wherein the purchase information record persists in a data store operably coupled with the at least one processor and wherein the purchase information record is redeemable at least until each of the healthcare services in the bundled plurality of individual services is redeemed.

10. The method of claim 1, wherein the method further comprises receiving, by the at least one processor, a request comprising machine readable information uniquely associated with the machine-readable identifier.

11. The method of claim 10, wherein the request further comprises a request to redeem the purchase information record with respect to at least one individual service of the bundled plurality of individual services.

12. The method of claim 10, wherein the request further comprises a request to determine the individual redemption status of at least one individual service of the bundled plurality of individual services.

13. The method of claim 10, wherein the method further comprises updating, by the at least one processor, the individual redemption status of at least one individual service of the bundled plurality of individual services in the purchase information record to indicate the at least one individual service has been redeemed.

14. The method of claim 1, wherein the machine learning model further comprises at least one neural network.

15. The method of claim 14, wherein the at least one neural network further comprises a deep-learning neural network.

16. The method of claim 14, wherein the at least one neural network is a trained neural network that was trained based on supervised training to predict likely patient conditions based on the patient information input.

17. The method of claim 16, wherein the method further comprises recommending, by the at least one processor, services or tests medically indicated for predicted likely conditions.

18. The method of claim 16, wherein the supervised training further comprised using a training data set comprising a plurality of time-series healthcare outcome data points sampled during a past time period from a plurality of patient healthcare episodes.

19. The method of claim 18, wherein the supervised training further comprised training the at least one neural network to determine a probability distribution of patient condition trends for a future time period using the training data set and labeled test data.

20. The method of claim 19, wherein each healthcare outcome data point of the plurality of time-series healthcare outcome data points further comprises information identifying services performed, service date, and a patient condition data point comprising current patient condition before the bundled services were performed and patient condition after the bundled plurality of individual services were performed.

21. The method of claim 19, wherein each patient healthcare episode of the plurality of patient healthcare episodes further comprises care for a condition distributed over a plurality of patient encounters during a period of time.

22. The method of claim 21, wherein the at least one neural network further comprises a plurality of neural network inputs.

23. The method of claim 22, wherein healthcare outcome data points and patient condition data points from each patient healthcare episode of the plurality of patient healthcare episodes are applied respectively to the plurality of neural network inputs.

24. The method of claim 23, wherein each time-series patient condition data point represents a single patient care encounter and each neural network input of the plurality of neural network inputs receives time-series data points from one episode.

25. The method of claim 24, wherein each patient condition data point further comprises patient condition data prior to and current with the patient care encounter.

26. The method of claim 25, wherein the supervised training further comprised creating the training data set.

27. The method of claim 26, wherein creating the training data set further comprised labeling patient condition changes with a label determined for each patient care encounter in a time-series of encounters as stable, deteriorating, improving, or reached goal.

28. The method of claim 27, wherein the label is determined based on comparing patient condition data prior to and current with the patient care encounter to determine a patient condition trend.

29. The method of claim 28, wherein the supervised training further comprised using the labeled time-series patient condition data for the past time period to train the at least one neural network to determine the probability distribution of patient condition trends for the future time period.

30. The method of claim 1, wherein the method further comprises offering or acquiring one or more smart contract for the at least one recommended healthcare service.

* * * * *